United States Patent
Burton et al.

(10) Patent No.: US 10,813,354 B2
(45) Date of Patent: Oct. 27, 2020

(54) HERBICIDAL PYRIDAZINONE COMPOUNDS

(71) Applicant: SYNGENTA PARTICIPATIONS AG, Basel (CH)

(72) Inventors: Paul Matthew Burton, Bracknell (GB); Steven Gaulier, Bracknell (GB); Paula Rocha Rzepa, Bracknell (GB); Melanie Jayne Watkins, Bracknell (GB); Mary Bernadette Aspinall, Bracknell (GB); Edward John Emmett, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 27 days.

(21) Appl. No.: 16/093,338

(22) PCT Filed: Apr. 13, 2017

(86) PCT No.: PCT/EP2017/058915
§ 371 (c)(1),
(2) Date: Oct. 12, 2018

(87) PCT Pub. No.: WO2017/178582
PCT Pub. Date: Oct. 19, 2017

(65) Prior Publication Data
US 2019/0124926 A1    May 2, 2019

(30) Foreign Application Priority Data

Apr. 15, 2016 (GB) .................................. 1606613.6
Oct. 20, 2016 (GB) .................................. 1617766.9

(51) Int. Cl.
| | | |
|---|---|---|
| *A01N 43/58* | (2006.01) | |
| *C07D 237/14* | (2006.01) | |
| *C07D 403/06* | (2006.01) | |
| *C07D 405/06* | (2006.01) | |
| *C07D 407/06* | (2006.01) | |

(52) U.S. Cl.
CPC ........... *A01N 43/58* (2013.01); *C07D 237/14* (2013.01); *C07D 403/06* (2013.01); *C07D 405/06* (2013.01); *C07D 407/06* (2013.01)

(58) Field of Classification Search
CPC .... A01N 43/58; C07D 237/14; C07D 403/06; C07D 407/06; C07D 405/06
See application file for complete search history.

(56) References Cited

U.S. PATENT DOCUMENTS 3,063,463 A    11/1962   Gföll

FOREIGN PATENT DOCUMENTS

| | | |
|---|---|---|
| DE | 1123934 B | 2/1962 |
| DE | 4423934 A1 | 3/1995 |
| WO | WO 99/52878 | * 10/1999 |
| WO | 2012136703 A1 | 10/2012 |
| WO | 2013139760 A1 | 9/2013 |

OTHER PUBLICATIONS

Derwent abstract 1999-620351, abstracting WO 99/52878 (Oct. 1999).*
Search Report issued by UKIPO dated Jan. 18, 2017 for GB 1606613.6.
International Search Report dated May 12, 2017 for PCT application PCT/EP2017/058915.

* cited by examiner

*Primary Examiner* — John Pak
(74) *Attorney, Agent, or Firm* — Baker & Hostetler LLP; Toni-Junell Herbert

(57) ABSTRACT

The present invention relates to compounds of Formula (I), or an agronomically acceptable salt of said compounds wherein $A^1$, $R^1$, $R^a$, $R^b$, $R^c$ and $R^d$ are as defined herein. The invention further relates to herbicidal compositions which comprise a compound of Formula (I), to intermediate compounds used to produce compounds of Formula (I), to processes for producing compounds of Formula (I) and to the use of compounds of Formula (I) for controlling weeds, in particular in crops of useful plants.

20 Claims, No Drawings

HERBICIDAL PYRIDAZINONE COMPOUNDS

CROSS-REFERENCE TO RELATED APPLICATIONS

This application is a 371 National Stage application of International Application No. PCT/EP2017/058915, filed Apr. 13, 2017, which claims priority to Great Britain Patent Application No. 1606613.6 filed Apr. 15, 2016 and Great Britain Patent Application No. 1617766.9, the entire contents of which applications are hereby incorporated by reference.

The present invention relates to novel herbicidal compounds, to processes for their preparation, to herbicidal compositions which comprise the novel compounds, and to their use for controlling weeds, in particular in crops of useful plants, or for inhibiting plant growth.

Herbicidal pyridazinone compounds are disclosed in WO 2012/136703. These compounds are shown to afford effective weed control with regard to a variety of problematic weed species. The present invention relates to novel herbicidal pyridazinone compounds which exhibit further improved properties. In particular, the compounds of the present invention exhibit improved crop selectivity. That is, they continue to provide effective levels of weed control, whilst exhibiting a reduction in undesirable crop phytotoxicity.

Thus, according to the present invention there is provided a compound of Formula (I):

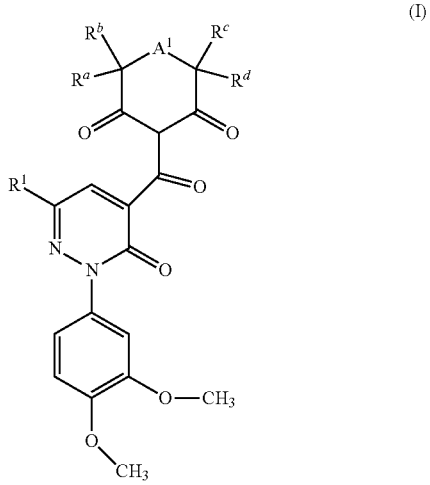

or an agronomically acceptable salt thereof,
wherein $R^1$ is selected from the group consisting of hydrogen, halogen, cyano, nitro, $C_1$-$C_6$alkyl-, $C_3$-$C_6$cycloalkyl-, $C_2$-$C_6$-alkenyl-, $C_2$-$C_6$alkynyl-, $C_1$-$C_6$haloalkyl-, $C_1$-$C_6$alkoxy-, $C_1$-$C_3$haloalkoxy-, $C_1$-$C_6$alkoxy-$C_1$-$C_3$alkyl-, $C_1$-$C_6$alkyl-S(O)p- and $C_1$-$C_6$haloalkyl-S(O)p-;

$A^1$ is selected from the group consisting of O, C(O) and $(CR^eR^f)$;

$R^a$, $R^b$, $R^c$, $R^d$, $R^e$ and $R^f$ are each independently selected from the group consisting of hydrogen and $C_1$-$C_4$alkyl- wherein $R^a$ and $R^c$ may together form a $C_1$-$C_3$alkylene chain; and p is 0, 1 or 2.

$C_1$-$C_6$alkyl- and $C_1$-$C_4$alkyl- includes, for example, methyl (Me, $CH_3$), ethyl (Et, $C_2H_5$), n-propyl (n-Pr), isopropyl (i-Pr), n-butyl (n-Bu), isobutyl (i-Bu), sec-butyl and tert-butyl (t-Bu).

$C_2$-$C_6$-alkenyl- includes, for example, —CH=$CH_2$ (vinyl) and —$CH_2$—CH=$CH_2$ (allyl).

$C_2$-$C_6$alkynyl- includes, for example, —C≡CH (ethynyl) and —$CH_2$—C≡CH (propargyl).

Halogen (or halo) includes, for example, fluorine, chlorine, bromine or iodine. The same correspondingly applies to halogen in the context of other definitions, such as haloalkyl.

$C_1$-$C_6$haloalkyl- includes, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoropropyl and 2,2,2-trichloroethyl, heptafluoro-n-propyl and perfluoro-n-hexyl.

$C_1$-$C_6$alkoxy- includes, for example, methoxy, ethoxy, propoxy, isopropoxy, n-butoxy, isobutoxy, sec-butoxy or tert-butoxy or a pentyloxy or hexyloxy isomer, preferably methoxy and ethoxy.

$C_1$-$C_3$haloalkoxy- includes, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) includes, for example, methylthio, ethylthio, propylthio, isopropylthio, n-butylthio, isobutylthio, sec-butylthio or tert-butylthio, preferably methylthio or ethylthio. $C_1$-$C_6$haloalkyl-S— (haloalkylthio) relates to halogenated derivatives thereof.

$C_1$-$C_6$alkyl-S(O)— (alkylsulfinyl) includes, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl. $C_1$-$C_6$haloalkyl-S(O)— (haloalkylsulfinyl) relates to halogenated derivatives thereof.

$C_1$-$C_6$alkyl-S(O)$_2$— (alkylsulfonyl) includes, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl. $C_1$-$C_6$haloalkyl-S(O)$_2$— (haloalkylsulfonyl) relates to halogenated derivatives thereof.

$C_1$-$C_6$alkoxy-$C_1$-$C_3$alkyl- includes, for example, methoxymethyl, methoxyethyl, ethoxymethyl, ethoxyethyl, n-propoxymethyl, n-propoxyethyl, isopropoxymethyl or isopropoxyethyl.

$C_3$-$C_6$cycloalkyl- includes, for example, cyclopropyl (c-propyl (c-Pr)), cyclobutyl (c-butyl (c-Bu)), cyclopentyl (c-pentyl) and cyclohexyl (c-hexyl).

In a preferred embodiment of the present invention there is provided a compound of Formula (I), wherein $R^1$ is $C_1$-$C_6$alkyl- (preferably methyl) or $C_3$-$C_6$cycloalkyl- (preferably cyclopropyl). In a more preferred embodiment $R^1$ is methyl or cyclopropyl.

In a preferred embodiment of the present invention there is provided a compound of Formula (I) wherein $A^1$ is $CR^eR^f$ and $R^e$ and $R^f$ are hydrogen.

In another preferred embodiment of the present invention there is provided a compound of Formula (I) wherein $A^1$ is $CR^eR^f$ and $R^a$, $R^b$, $R^c$, $R^d$, $R^e$ and $R^f$ are hydrogen.

In another preferred embodiment of the present invention there is provided a compound of Formula (I) wherein $A^1$ is $CR^eR^f$; $R^a$, $R^b$, $R^c$, $R^d$, and $R^e$ are hydrogen and $R^f$ is methyl.

In another preferred embodiment of the present invention there is provided a compound of Formula (I) wherein $A^1$ is $CR^eR^f$; $R^a$, $R^b$, $R^c$, $R^d$ are hydrogen and $R^e$ and $R^f$ are methyl.

In another preferred embodiment of the present invention there is provided a compound of Formula (I) wherein $A^1$ is $CR^eR^f$; $R^b$, $R^d$, $R^e$ and $R^f$ are hydrogen, and $R^a$ and $R^c$ together form an ethylene ($-CH_2-CH_2-$) chain.

In another preferred embodiment of the present invention there is provided a compound of Formula (I) wherein $A^1$ is $C=O$ and $R^a$, $R^b$, $R^e$ and $R^d$ are methyl.

In another preferred embodiment of the present invention there is provided a compound of Formula (I) wherein $A^1$ is O and $R^a$, $R^b$, $R^c$ and $R^d$ are methyl.

Compounds of Formula (I) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted or trisubstituted alkenes, these may be present in E or Z form or as mixtures of both in any proportion.

Furthermore, compounds of Formula (I) may be in equilibrium with alternative tautomeric forms. Thus, whilst compounds of Formula (I) are depicted in the keto form, they may also exist in the alternative enol form as depicted in Formula (I') below.

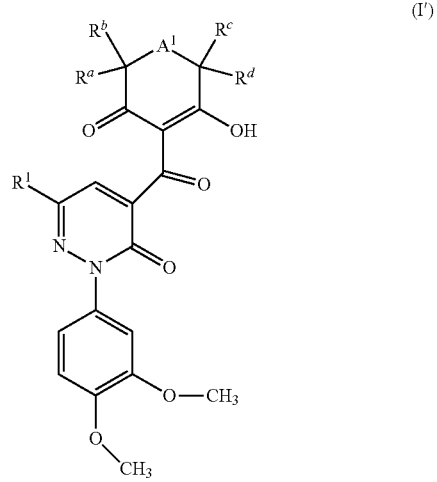

All tautomeric forms (single tautomer or mixtures thereof), racemic mixtures and single isomers are included within the scope of the present invention.

TABLE C1

Examples of herbicidal compounds of the present invention.

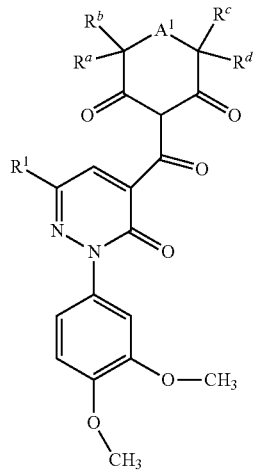

| Cmp | $A^1$ | $R^a$ | $R^c$ | $R^b$ | $R^d$ | $R^1$ | $^1$H NMR (400 MHz, CDCl$_3$) |
|---|---|---|---|---|---|---|---|
| 1.1 | CH$_2$ | —CH$_2$—CH$_2$— | | H | H | CH$_3$ | 16.19 (1H, s), 7.16-7.09 (3H, m), 6.93 (1H, d), 3.91 (6H, s), 3.11 (1H, t), 2.94 (1H, t), 2.42 (3H, s), 2.26-2.06 (3H, m), 2.04-1.98 (1H, m), 1.83 (1H, brm), 1.72 (1H, dt) |
| 1.2 | CHCH$_3$ | H | H | H | H | CH$_3$ | 16.07 (1H, s), 7.12 (1H, d), 7.08 (2H, m), 6.90 (1H, d), 3.89 (3H, s), 3.88 (3H, s), 2.76-2.71 (1H, m), 2.53-2.42 (2H, m), 2.40 (3H, s), 2.34-2.29 (1H, m), 2.19-2.12 (1H, m), 1.08 (3H, d). |
| 1.3 | CH$_2$ | H | H | H | H | CH$_3$ | 16.14 (1H, s), 7.13 (1H, dd), 7.09 (2H, m), 6.92 (1H, d), 3.90 (3H, s), 3.89 (3H, s), 2.73 (3H, t), 2.46 (3H, t), 2.41 (3H, s), 2.04 (2H, quintet). |
| 1.4 | C(CH$_3$)$_2$ | H | H | H | H | CH$_3$ | 16.14 (1H, s), 7.13-7.08 (3H, m), 6.90 (1H, s), 3.89 (3H, s), 3.88 (3H, s), 2.60 (2H, s), 2.90 (3H, s), 2.34 (2H, s), 1.10 (6H, s). |
| 1.5 | C=O | CH$_3$ | CH$_3$ | CH$_3$ | CH$_3$ | CH$_3$ | 7.22 (s, 1H), 7.13-7.02 (m, 2H), 6.92 (d, J = 8.6 Hz, 1H), 3.91 (s, 3H), 3.89 (s, 3H), 2.43 (s, 3H), 1.53 (s, 6H), 1.40 (br. s., 6H) |

TABLE C1-continued

Examples of herbicidal compounds of the present invention.

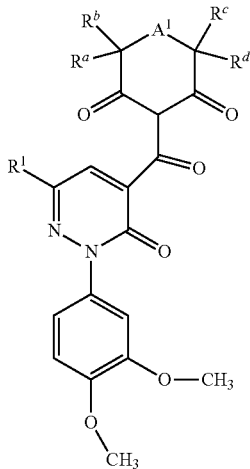

| Cmp | $A^1$ | $R^a$ | $R^c$ | $R^b$ | $R^d$ | $R^1$ | $^1$H NMR (400 MHz, CDCl$_3$) |
|---|---|---|---|---|---|---|---|
| 1.6 | CHC$_2$H$_5$ | H | H | H | H | CH$_3$ | 16.10 (br. s., 1 H) 7.04-7.26 (m, 3 H) 6.92 (d, 1 H) 3.90 (s, 3 H) 3.89 (s, 3 H) 2.76 (brs., 1 H) 2.55 (brs, 1 H) 2.33-2.50 (m, 4 H) 2.13 (brs, 2 H) 1.34-1.51 (m, 2 H) 0.94 (t, 3 H) |
| 1.7 | CH$_2$ | CH$_3$ | CH$_3$ | CH$_3$ | CH$_3$ | CH$_3$ | |
| 1.8 | CHCH$_3$ | H | H | H | H | cPr | 7.14-7.10 (2H, m), 6.98 (1H, s), 6.89 (1H, d), 3.89 (3H, s), 3.87 (3H, s), 2.75-2.71 (1H, m), 2.53-2.39 (2H, m), 2.32-2.26 (1H, m), 2.18-2.12 (1H, m), 1.97-1.90 (1H, m), 1.08 (3H, d), 0.99-0.95 (2H, m), 0.93-0.87 (2H, m). |
| 1.9 | CH$_2$ | —CH$_2$—CH$_2$— | | H | H | cPr | 16.18 (1H, s), 7.14-7.10 (2H, m), 6.96 (1H, s), 6.89 (1H, d), 3.89 (3H, s), 3.88 (3H, s), 3.08 (1H, t), 2.91 (1H, t), 2.23-1.89 (5H, m), 1.86-1.77 (1H, m), 1.69 (1H, dt), 1.01-0.94 (2H, m), 0.92-0.87 (2H, m). |
| 1.10 | C(CH$_3$)$_2$ | H | H | H | H | cPr | 16.15 (1H, s), 7.16-7.10 (2H, m), 7.00 (1H, s), 6.88 (1H, d), 3.89 (3H, s), 3.87 (3H, s), 2.59 (2H, s), 2.33 (2H, s), 1.97-1.90 (1H, m), 1.09 (6H, s), 1.01-0.95 (2H, m), 0.93-0.89 (2H, m). |
| 1.11 | C=O | CH$_3$ | CH$_3$ | CH$_3$ | CH$_3$ | cPr | 7.13 (s, 1H), 7.12-7.06 (m, 2H), 6.91 (d, J = 8.6 Hz, 1H), 3.91 (s, 3H) 3.88 (s, 3H), 2.00-1.92 (m, 1H), 1.52 (br. s., 6H), 1.40 (br. s., 6H), 1.05-0.98 (m, 2H), 0.98-0.91 (m, 2H). |
| 1.12 | CH$_2$ | H | H | H | H | cPr | 16.16 (1H, s), 7.14-7.10 (2H, m), 6.98 (1H, s), 6.89 (1H, d), 3.89 (3H, s), 3.87 (3H, s), 2.71 (2H, t), 2.44 (2H, t), 2.06-2.00 (2H, m), 1.97-1.91 (1H, m), 1.01-0.95 (2H, m), 0.93-0.90 (2H, m). |
| 1.13 | O | CH$_3$ | CH$_3$ | CH$_3$ | CH$_3$ | CH$_3$ | 7.15 (s, 1H), 7.10 (m, 2H), 6.90 (d, 2H), 3.90 (s, 3H), 3.88 (s, 3H), 2.41 (s, 3H), 1.58 (s, 6H), 1.42 (s, 6H) |
| 1.14 | O | CH$_3$ | CH$_3$ | CH$_3$ | CH$_3$ | cPr | 7.27 (s, 1H), 7.11 (d, 2H), 6.90 (d, 2H), 3.92 (s, 3H), 3.87 (s, 3H), 1.95 (m, 1H), 1.58 (s, 6H), 1.41 (s, 6H), 1.01 (m, 2H), 0.94 (m, 2H) |

The present invention also provides agronomically acceptable salts of compounds of Formula (I). Salts that the compounds of Formula (I) may form with amines, including primary, secondary and tertiary amines (for example ammonia, dimethylamine and triethylamine), alkali metal and alkaline earth metal bases, transition metals or quaternary ammonium bases are preferred. Aluminium, calcium, cobalt, copper (copper (I), copper (II)), iron (iron (II), iron (III)), magnesium, potassium, sodium or zinc salts of compounds of Formula (I) are particularly preferred; copper, potassium and sodium being especially preferred.

The compounds of Formula (I) according to the invention can be used as herbicides by themselves, but they are generally formulated into herbicidal compositions using co-formulants, such as carriers, solvents, surface-active agents (SAA) and adjuvants. Thus, the present invention further provides a herbicidal composition comprising a herbicidal compound according to any one of the previous claims and an agriculturally acceptable co-formulant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a co-formulant which preferably includes from 0 to 25% by weight of a surface-active substance.

The compositions can be chosen from a number of formulation types. These include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a soluble powder (SP), a wettable powder (WP), a ZC (combination of SC and CS) and a soluble granule (SG). The formulation type chosen in any instance will depend upon the particular purpose envisaged and the physical, chemical and biological properties of the compound of Formula (I) and any additional ingredient.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol) and dimethyl amides of fatty acids (such as $C_8$-$C_{10}$ fatty acid dimethylamide). An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SAAs, under high shear, to produce an emulsion. Suitable solvents for use in EWs include vegetable oils, aromatic solvents (such as alkylbenzenes or alkylnaphthalenes) and other appropriate organic solvents which have a low solubility in water.

Microemulsions (ME) may be prepared by mixing water with a blend of one or more solvents with one or more SAAs, to produce spontaneously a thermodynamically stable isotropic liquid formulation. A compound of Formula (I) is present initially in either the water or the solvent/SAA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I). A compound of Formula (I) may also be formulated in a biodegradable polymeric matrix to provide a slow, controlled release of the compound.

Soluble concentrate (SL) may be prepared by dissolving the active ingredient in an aqueous liquid which optionally comprises wetting agent(s) and/or buffer(s).

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SAAs), spray additives based on oils, for example certain mineral oils or natural plant oils (such as soy bean and rape seed oil), modified plant oils such as methylated rape seed oil (MRSO), and blends of these with other bio-enhancing adjuvants (ingredients which may aid or modify the action of a compound of Formula (I).

Examples of co-formulants include:—

Wetting agents, dispersing agents and emulsifying agents may be SAAs of the cationic, anionic, amphoteric or non-ionic type.

Suitable SAAs of the cationic type include quaternary ammonium compounds (for example cetyltrimethyl ammonium bromide), imidazolines and amine salts.

Suitable anionic SAAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates, lignosulphonates and phosphates/sulphates of tristyrylphenols.

Suitable SAAs of the amphoteric type include betaines, propionates and glycinates.

Suitable SAAs of the non-ionic type include condensation products of alkylene oxides, such as ethylene oxide, propylene oxide, butylene oxide or mixtures thereof, with fatty alcohols (such as oleyl alcohol or cetyl alcohol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); lecithins and sorbitans and esters thereof, alkyl polyglycosides and tristyrylphenols.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise one or more additional pesticides. For example, the compounds according to the invention can also be used in combination with other herbicides or plant growth regulators. Thus, in a preferred embodiment there is provided a herbicidal composition comprising (A) a compound of Formula (I) and (B) one or more herbicides selected from the group consisting of acetochlor, aciflurofen (aciflurofen-sodium), aclonifen, alachlor, alloxydim, ametryn, amicarbazone, amidosulfuron, aminocyclopyrachlor, aminopyralid, amitrole, anilifos, asulam, atrazine, beflubutamid, benefin, benfluralin, bensulfuron (including bensulfuron-methyl), bentazone, bicyclopyrone, bifenox, bispyribac-sodium, bromacil, bromoxynil, butachlor, butroxydim, butafenacil, cafenstrole, carfentrazone (including carfentrazone-ethyl), chloransulam, chlorimuron (including chlorimuron-ethyl), chlorotoluron, chlorsulfuron, cinosulfuron, cinidon (including cinidon-ethyl), clethodim, clodinafop (including clodinafop-propargyl), clomazone, clopyralid, cycloxydim, cyhalofop (including cyhalofop-butyl), 2,4-D (including the choline salt and 2-ethylhexyl ester thereof), daimuron, desmedipham, dicamba (including the aluminum, aminopropyl, bis-aminopropylmethyl, choline, dichlorprop, diglycolamine, dimethylamine, dimethylammonium, potassium and sodium salts thereof), diclofop (including diclofop-methyl), diclosulam, difenzoquat, diflufenican, diflufenzopyr, dimethachlor, dimethenamid-P, diquat dibromide, diuron, EPTC, esprocarb, ethametsulfuron, ethofumesate, fenoxaprop (including fenoxaprop-P-ethyl), fenquinotrione, flazasulfuron, florasulam, fluazifop (including fluazifop-P-butyl), flucarbazone (including flucarbazone-sodium), flufenacet, flumetralin, flumetsulam, fluormeturon, fluoroglycofen, flumioxazin, flupyrsulfuron (including flupyrsulfuron-methyl-sodium), fluroxypyr (including fluroxypyr-meptyl), flurtamone, fluthiacet (including fluthiacet-methyl), fomesafen, foramsulfuron, glufosinate (including the ammonium salt thereof), glyphosate (including the diammonium, isopropylammonium and potassium salts thereof), halauxifen (including halauxifen-methyl), halosulfuron (including halosulfuron-methyl), haloxyfop (including haloxyfop-methyl), hexazinone, imazamethabenz, imazamox, imazapic, imazapyr, imazaquin, imazethapyr, indaziflam, iodosulfuron (including iodosulfuron-methyl-sodium), iofensulfuron (including iofensulfuron-sodium), ioxynil, ipfencarbazone, isoproturon, isoxaben, isoxaflutole, lactofen, linuron, MCPA, mecoprop-P, mefenacet, mesosulfuron (including mesosulfuron-methyl), mesotrione, metamitron, metazachlor, metobromuron, metolachlor, metoxuron, metribuzin, metsulfuron, molinate, napropamide, nicosulfuron, norflurazon, orthosulfamuron, oxadiargyl, oxadiazon, oxasulfuron, oxaziclomefone, oxyfluorfen, paraquat dichloride, pendimethalin, penoxsulam, pethoxamid, phenmedipham, picloram, picolinafen, pinoxaden, pretilachlor, primisulfuron-methyl, prodiamine, prometryn, propachlor, propanil, propaquizafop, propham, propoxycarbazone, propyzamide, prosulfocarb, prosulfuron, pyraflufen (including pyraflufen-ethyl), pyrasulfotole, pyrazolynate, pyrazosulfuron (including pyrazosulfuron-ethyl), pyribenzoxim, pyridate, pyriftalid, pyrithiobac-sodium, pyroxasulfone, pyroxsulam, quinclorac, quizalofop (including quizalofop-P-ethyl), rimsulfuron, saflufenacil, sethoxydim, simetryn, S-metolachlor, sulcotrione, sulfentrazone, sulfometuron (including sulfometuron-methyl), sulfosulfuron, tebuthiuron, tefuryltrione, tembotrione, tepraloxydim, terbuthylazine, terbutryn, thiencarbazone, thifensulfuron, tiafenacil, tolpyralate, topramezone, tralkoxydim, triafamone, triallate, triasulfuron, tribenuron (including tribenuron-methyl), triclopyr, trifloxysulfuron (including trifloxysulfuron-sodium), trifludimoxazin, trifluralin, tritosulfuron, 4-amino-3-chloro-6-(4-chloro-2-fluoro-3-methoxyphenyl)-5-fluoropyridine-2-carboxylate (Compound B1), 4-hydroxy-1-methoxy-5-methyl-3-[4-(trifluoromethyl)-2-pyridyl]imidazolidin-2-one (Compound B2), 4-hydroxy-1,5-dimethyl-3-[4-(trifluoromethyl)-2-pyridyl]imidazolidin-2-one (Compound B3), 5-ethoxy-4-hydroxy-1-methyl-3-[4-(trifluoromethyl)-2-pyridyl]imidazolidin-2-one (Compound B4), 4-hydroxy-1-methyl-3-[4-(trifluoromethyl)-2-pyridyl]imidazolidin-2-one (Compound B5), 4-hydroxy-1,5-dimethyl-3-[1-methyl-5-(trifluoromethyl)pyrazol-3-yl]imidazolidin-2-one (Compound B6), (4R)1-(5-tert-butylisoxazol-3-yl)-4-ethoxy-5-hydroxy-3-methyl-imidazo lidin-2-one (Compound B7), a compound of formula B8,

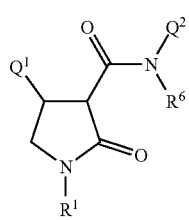

B8 wherein,
$R^1$ is H, $C_1$-$C_6$alkyl, $C_1$-$C_6$ haloalkyl or $C_4$-$C_8$ cycloalkyl;
$R^6$ is H, $C_1$-$C_6$alkyl, or $C_1$-$C_6$alkoxy;
$Q^1$ is an optionally substituted ring system, selected from the group consisting of phenyl, thienyl, pyridinyl, benzodioxolyl, naphthyl, naphthalenyl, benzofuranyl, furanyl, benzothiophenyl, and pyrazolyl, wherein when substituted said ring system is substituted by 1 to 3 $R^4$;
$Q^2$ is an optionally substituted ring system, selected from the group consisting of phenyl, pyridinyl, benzodioxolyl, pyridinone, thiadazolyl, thiazolyl, and oxazolyl, wherein when substituted said ring system is substituted by 1 to 3 $R^5$;
each $R^4$ is independently halogen, $C_1$-$C_6$alkyl, $C_1$-$C_6$haloalkyl, $C_1$-$C_6$alkoxy, $C_1$-$C_6$haloalkoxy, $C_3$-$C_5$cycloalkyl, cyano, $C_1$-$C_6$alkylthio, $C_1$-$C_6$alkylsulphinyl, $C_1$-$C_6$alkylsulphonyl, $SF_5$, $NHR^8$, phenyl optionally substituted by 1-3 $R^7$, or pyrazolyl optionally substituted by 1-3 $R^7$;
each $R^5$ is independently halogen, $C_1$-$C_6$alkyl, $C_1$-$C_6$haloalkyl, $C_1$-$C_6$alkoxy, $C_1$-$C_6$haloalkoxy, cyano, nitro, $C_1$-$C_6$alkylthio, $C_1$-$C_6$alkylsulphinyl, or $C_1$-$C_6$alkylsulphonyl;
each $R^7$ is independently $C_1$-$C_6$alkyl, halogen, or $C_1$-$C_6$haloalkyl; and
$R^8$ is $C_1$-$C_4$alkoxycarbonyl;
and a compound of formula B9,

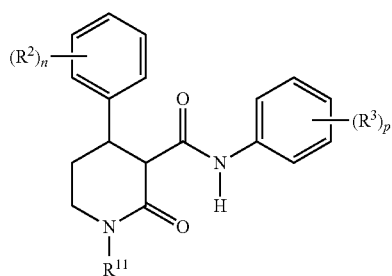

B9 wherein,
$R^{11}$ is H, $C_1$-$C_6$alkyl, $C_1$-$C_6$ haloalkyl or $C_4$-$C_8$ cycloalkyl;

n is an integer of 0, 1, 2, or 3;
p is an integer of 0, 1, 2, or 3;
each $R^2$ is independently halogen, $C_1$-$C_6$haloalkyl, or $C_1$-$C_6$haloalkoxy; and
each $R^3$ is independently halogen, $C_1$-$C_6$haloalkyl, $C_1$-$C_6$ haloalkoxy.

More preferably, (B) is one or more herbicides selected from the group consisting of acetochlor, alachlor, ametryn, amicarbazone, atrazine, bicyclopyrone, bromoxynil, butachlor, chlorotoluron, clodinafop-propargyl, clopyralid, 2,4-D (including the choline salt and 2-ethylhexyl ester thereof), dicamba (including the aluminium, aminopropyl, bis-aminopropylmethyl, choline, diglycolamine, dimethylamine, dimethylammonium, potassium and sodium salts thereof), diflufenican, dimethachlor, dimethenamid-P, diuron, fenoxaprop-P-ethyl, fenquinotrione, florasulam, fluazifop-P-butyl, fluroxypyr-meptyl, flucarbazone-sodium, flufenacet, foramsulfuron, glufosinate (including the ammonium salt thereof), fomesafen, glyphosate (including the diammonium, isopropylammonium and potassium salts thereof), halauxifen-methyl, iodosulfuron-methyl-sodium, isoxaflutole, isoproturon, linuron, MCPA, mecoprop-P, mesosulfuron-methyl, mesotrione, metazachlor, S-metolachlor, metribuzin, metsulfuron, nicosulfuron, pendimethalin, pethoxamid, pinoxaden, prometryn, prosulfocarb, prosulfuron, pyrasulfatole, pyridate, pyroxasulfone, pyroxsulam, rimsulfuron, simazine, sulcotrione, sulfentrazone, tembotrione, terbuthylazine, terbutryn, thiencarbazone, tolpyralate, topramezone, triasulfuron and trifludimoxazin.

Even more preferably, (B) is one or more herbicides selected from the group consisting of atrazine, bicyclopyrone, bromoxynil, clodinafop-propargyl, diflufenican, fenoxaprop-P-ethyl, florasulam, flufenacet, fluroxypyr-meptyl, glufosinate (including the ammonium salt thereof), glyphosate (including the diammonium, isopropylammonium and potassium salts thereof), halauxifen-methyl, iodosulfuron-methyl-sodium, MCPA, mesosulfuron-methyl, mesotrione, metribuzin, metsulfuron, nicosulfuron, S-metolachlor, pinoxaden, prosulfocarb, pyroxsulam and terbuthylazine.

In one embodiment, wherein component B is a compound of formula B8, it is preferred that $R^{11}$ is H, $C_1$-$C_6$ alkyl or $C_1$-$C_6$haloalkyl, more preferably methyl, ethyl or $CHF_2$, and more preferably still, H or methyl.

Preferably $R^6$ is H. Preferably $Q^1$ is either a phenyl ring or a pyridinyl ring, each of which is optionally substituted by 1 to 3 $R^4$. Preferably $Q^1$ is a phenyl ring substituted by 1 to 2 $R^4$. Preferably $Q^2$ is a phenyl ring, optionally substituted by 1 to 3 $R^5$. More preferably $Q^1$ is phenyl substituted by 1-3 $R^5$. Preferably each $R^4$ is independently halogen, $C_1$-$C_4$ alkyl, $C_1$-$C_3$ haloalkyl, $C_1$-$C_3$alkoxy, or $C_1$-$C_3$haloalkoxy; more preferably chloro, fluoro, bromo, $C_1$-$C_2$haloalkyl, $C_1$-$C_2$haloalkoxy, or $C_1$-$C_2$alkoxy. Preferably each $R^5$ is independently halogen, $C_1$-$C_4$ alkyl, $C_1$-$C_3$ haloalkyl, $C_1$-$C_3$alkoxy, or $C_1$-$C_3$haloalkoxy; more preferably chloro, fluoro, bromo, $C_1$-$C_2$haloalkyl, $C_1$-$C_2$haloalkoxy, or $C_1$-$C_2$alkoxy; more preferably still fluoro.

Particularly preferred compounds of formula B8 for use as component B in compositions of the invention are shown as compounds B801 to B815 below in Table B8.

TABLE B8

Compound of formula (B8) for use in compositions described herein.

| Compound Name | | Structure |
|---|---|---|
| B801 | N-(2-fluorophenyl)-2-oxo-4-[3-(trifluoromethyl)phenyl]pyrrolidine-3-carboxamide | 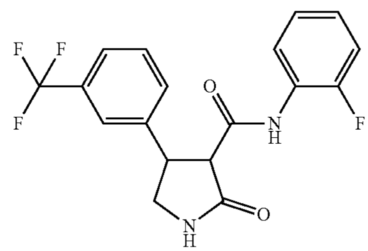 [SMILES: O=C1NCC(c2cccc(C(F)(F)F)c2)C1C(=O)Nc1ccccc1F] |
| B802 | N-(2,3-difluorophenyl)-2-oxo-4-[3-(trifluoromethyl)phenyl]pyrrolidine-3-carboxamide | 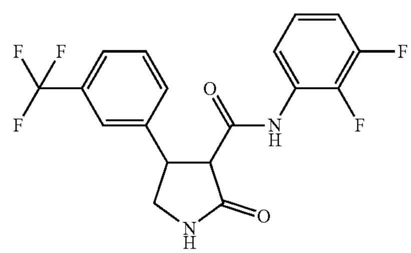 [SMILES: O=C1NCC(c2cccc(C(F)(F)F)c2)C1C(=O)Nc1cccc(F)c1F] |
| B803 | 2-oxo-4-[3-(trifluoromethyl)phenyl]-N-(2,3,4-trifluorophenyl)pyrrolidine-3-carboxamide | 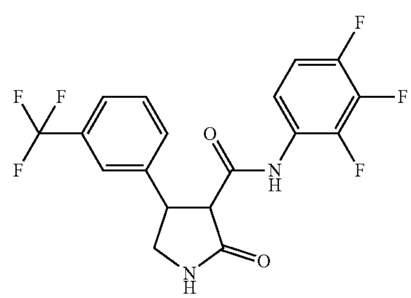 [SMILES: O=C1NCC(c2cccc(C(F)(F)F)c2)C1C(=O)Nc1ccc(F)c(F)c1F] |
| B804 | N-(2-fluorophenyl)-1-methyl-2-oxo-4-[3-(trifluoromethyl)phenyl]pyrrolidine-3-carboxamide | 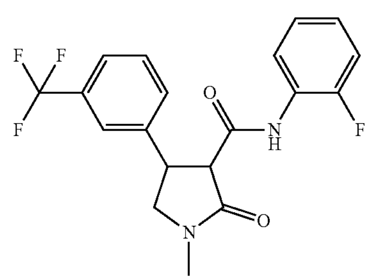 [SMILES: CN1CC(c2cccc(C(F)(F)F)c2)C(C(=O)Nc2ccccc2F)C1=O] |
| B805 | N-(2-fluorophenyl)-2-oxo-4-[4-(trifluoromethyl)phenyl]pyrrolidine-3-carboxamide | 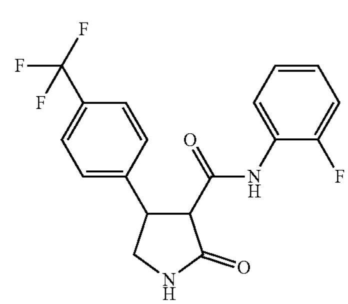 [SMILES: O=C1NCC(c2ccc(C(F)(F)F)cc2)C1C(=O)Nc1ccccc1F] |

TABLE B8-continued

Compound of formula (B8) for use in compositions described herein.

| Compound | Name | Structure |
|---|---|---|
| B806 | N-(2-fluorophenyl)-1-methyl-2-oxo-4-[4-(trifluoromethyl)phenyl]pyrrolidine-3-carboxamide | 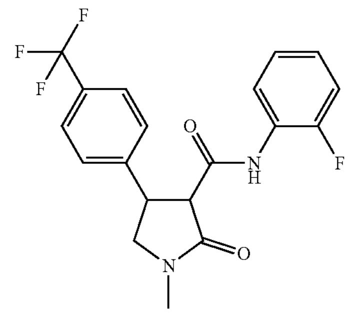 [SMILES: CN1CC(c2ccc(C(F)(F)F)cc2)C(C(=O)Nc2ccccc2F)C1=O] |
| B807 | N-(2,3-difluorophenyl)-2-oxo-4-[4-(trifluoromethyl)phenyl]pyrrolidine-3-carboxamide | 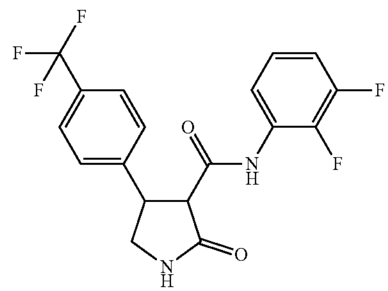 [SMILES: O=C1NCC(c2ccc(C(F)(F)F)cc2)C1C(=O)Nc1cccc(F)c1F] |
| B808 | N-(2,3-difluorophenyl)-1-methyl-2-oxo-4-[4-(trifluoromethyl)phenyl]pyrrolidine-3-carboxamide | 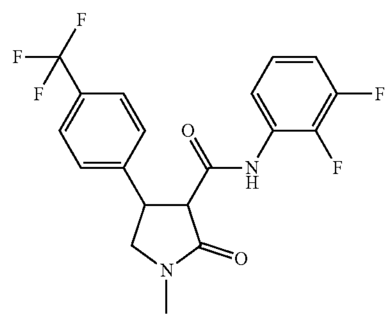 [SMILES: CN1CC(c2ccc(C(F)(F)F)cc2)C(C(=O)Nc2cccc(F)c2F)C1=O] |
| B809 | 2-oxo-4-[4-(trifluoromethyl)phenyl]-N-(2,3,4-trifluorophenyl)pyrrolidine-3-carboxamide | 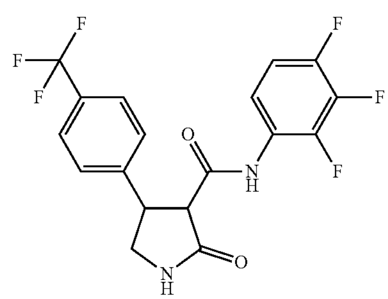 [SMILES: O=C1NCC(c2ccc(C(F)(F)F)cc2)C1C(=O)Nc1ccc(F)c(F)c1F] |
| B810 | N-(2-fluorophenyl)-4-(4-fluorophenyl)-1-methyl-2-oxo-pyrrolidine-3-carboxamide | 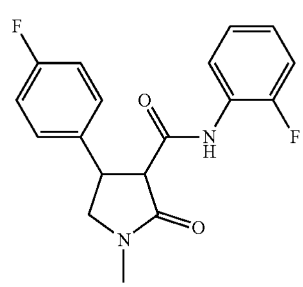 [SMILES: CN1CC(c2ccc(F)cc2)C(C(=O)Nc2ccccc2F)C1=O] |

TABLE B8-continued

Compound of formula (B8) for use in compositions described herein.

| Compound Name | | Structure |
|---|---|---|
| B811 | N-(2,3-difluorophenyl)-4-(3,4-difluorophenyl)-2-oxo-pyrrolidine-3-carboxamide | 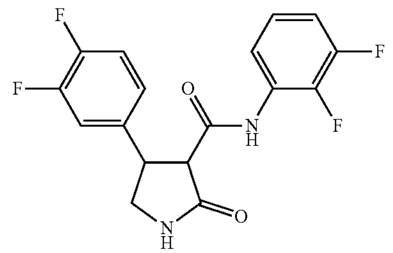 [SMILES: O=C1NCC(c2ccc(F)c(F)c2)C1C(=O)Nc1cccc(F)c1F] |
| B812 | 4-(3,4-difluorophenyl)-N-(2-fluorophenyl)-2-oxo-pyrrolidine-3-carboxamide | 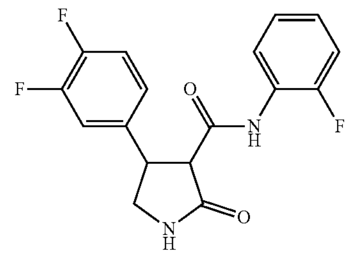 [SMILES: O=C1NCC(c2ccc(F)c(F)c2)C1C(=O)Nc1ccccc1F] |
| B813 | N-(2,4-difluorophenyl)-4-(3,5-difluorophenyl)-2-oxo-pyrrolidine-3-carboxamide | 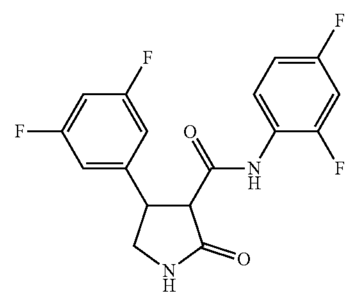 [SMILES: O=C1NCC(c2cc(F)cc(F)c2)C1C(=O)Nc1ccc(F)cc1F] |
| B814 | N-(2,3-difluorophenyl)-4-(3-isopropylphenyl)-2-oxo-pyrrolidine-3-carboxamide | 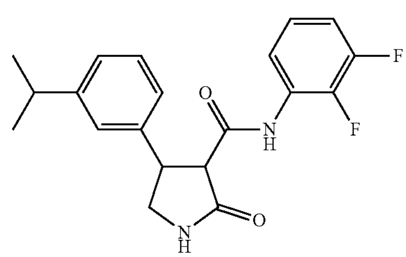 [SMILES: CC(C)c1cccc(C2CNC(=O)C2C(=O)Nc2cccc(F)c2F)c1] |
| B815 | N-(2,3-difluorophenyl)-2-oxo-4-[6-(trifluoromethyl)-3-pyridyl]pyrrolidine-3-carboxamide | 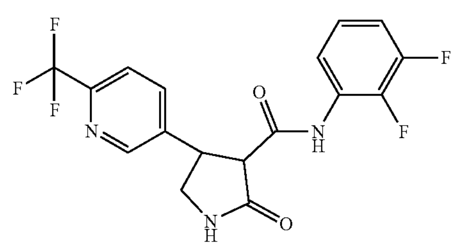 [SMILES: O=C1NCC(c2ccc(C(F)(F)F)nc2)C1C(=O)Nc1cccc(F)c1F] |

Compounds of formula B8 as described herein may be made as described in WO2015/084796 and WO 2016/094117.

In a further embodiment wherein component B is a compound of formula B9 it is preferred that p is 1, 2, or 3, more preferably 1 or 2. Preferably n is 1, 2 or 3, more preferably 1 or 2. Preferably $R^1$ is H or $C_1$-$C_6$alkyl, more preferably H or methyl. In one set of embodiments $R^{11}$ is H.

Preferably each $R^2$ is independently chloro, fluoro, $C_1$-$C_3$haloalkyl, or $C_1$-$C_3$haloalkoxy, more preferably chloro, fluoro, $C_1$-fluoroalkyl (i.e. fluoromethyl, difluoromethyl, trifluoromethyl) $C_1$-fluoroalkoxy (i.e. trifluoromethoxy, difluoromethoxy, fluoromethoxy). Preferably each $R^3$ is independently chloro, fluoro, $C_1$-$C_3$haloalkyl, or $C_1$-$C_3$haloalkoxy, more preferably chloro, fluoro, $C_1$-fluoroalkyl (i.e. fluoromethyl, difluoromethyl, trifluoromethyl)

$C_1$-fluoroalkoxy (i.e. trifluoromethoxy, difluoromethoxy, fluoromethoxy). Particularly preferred compounds of formula B9 for use as component B in compositions of the invention are shown below in Table B9.

TABLE B9

Compound of formula B9 for use in compositions described herein (unless otherwise stated, all compounds are in racemic form).

| Compound | Name | Structure |
|---|---|---|
| B901 | 4-(3,4-difluorophenyl)-2-oxo-N-[2-(trifluoromethyl)phenyl]piperidine-3-carboxamide | 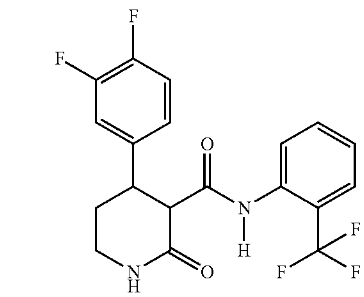 [SMILES: O=C1NCCC(c2ccc(F)c(F)c2)C1C(=O)Nc1ccccc1C(F)(F)F] |
| B902 | N-(2,3-difluorophenyl)-2-oxo-4-[3-(trifluoromethyl)phenyl]piperidine-3-carboxamide | 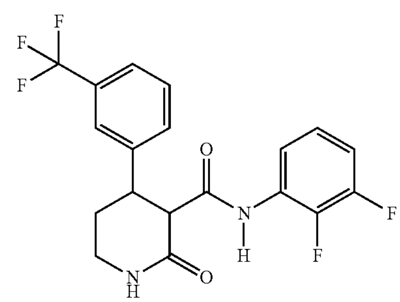 [SMILES: O=C1NCCC(c2cccc(C(F)(F)F)c2)C1C(=O)Nc1cccc(F)c1F] |
| B903 | 2-oxo-N-[2-(trifluoromethyl)phenyl]-4-[3-(trifluoromethyl)phenyl]piperidine-3-carboxamide | 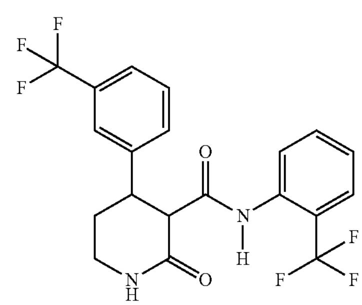 [SMILES: O=C1NCCC(c2cccc(C(F)(F)F)c2)C1C(=O)Nc1ccccc1C(F)(F)F] |
| B904 | N-(2-chlorophenyl)-2-oxo-4-[4-(trifluoromethyl)phenyl]piperidine-3-carboxamide | 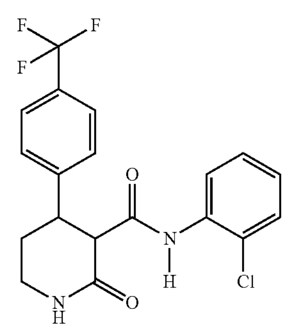 [SMILES: O=C1NCCC(c2ccc(C(F)(F)F)cc2)C1C(=O)Nc1ccccc1Cl] |

TABLE B9-continued

Compound of formula B9 for use in compositions described herein (unless otherwise stated, all compounds are in racemic form).

| Compound | Name | Structure |
| --- | --- | --- |
| B905 | N-(2-fluorophenyl)-2-oxo-4-[4-(trifluoromethyl)phenyl]piperidine-3-carboxamide | 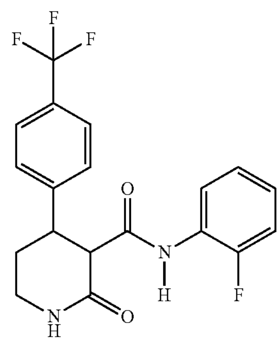 [SMILES: O=C1NCCC(c2ccc(C(F)(F)F)cc2)C1C(=O)Nc1ccccc1F] |
| B906 | (3R,4S)-N-(2,3-difluorophenyl)-2-oxo-4-[3-(trifluoromethyl)phenyl]piperidine-3-carboxamide | 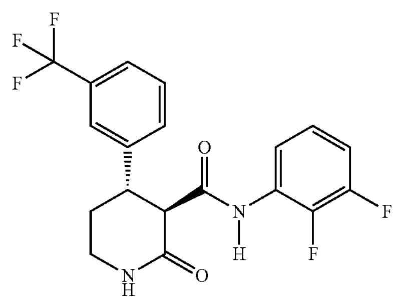 [SMILES: O=C1NCC[C@H](c2cccc(C(F)(F)F)c2)[C@H]1C(=O)Nc1cccc(F)c1F] |
| B907 | (3R,4S)-N-(2,3-difluorophenyl)-2-oxo-4-[4-(trifluoromethyl)phenyl]piperidine-3-carboxamide | 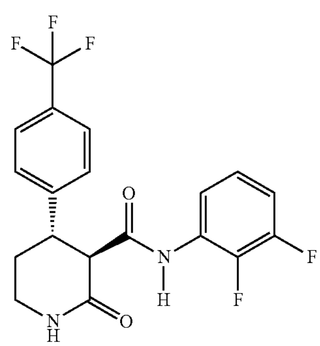 [SMILES: O=C1NCC[C@H](c2ccc(C(F)(F)F)cc2)[C@H]1C(=O)Nc1cccc(F)c1F] |
| B908 | (3R,4S)-N-(3-chloro-2-fluorophenyl)-2-oxo-4-[3-(trifluoromethyl)phenyl]piperidine-3-carboxamide | 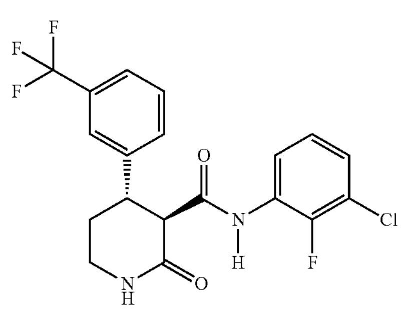 [SMILES: O=C1NCC[C@H](c2cccc(C(F)(F)F)c2)[C@H]1C(=O)Nc1cccc(Cl)c1F] |

TABLE B9-continued

Compound of formula B9 for use in compositions described herein (unless otherwise stated, all compounds are in racemic form).

| Compound | Name | Structure |
|---|---|---|
| B909 | (3R,4S)-2-oxo-4-[3-(trifluoromethyl)phenyl]-N-(2,3,4-trifluorophenyl)piperidine-3-carboxamide | 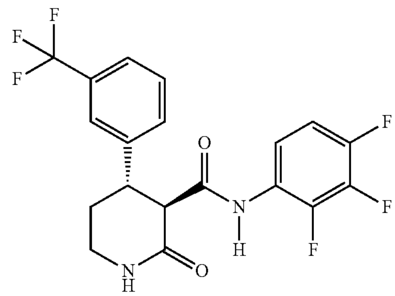 [SMILES: O=C1NCC[C@H](c2cccc(C(F)(F)F)c2)[C@H]1C(=O)Nc1ccc(F)c(F)c1F] |
| B910 | 4-(3-chlorophenyl)-N-(2,3-difluorophenyl)-2-oxo-piperidine-3-carboxamide | 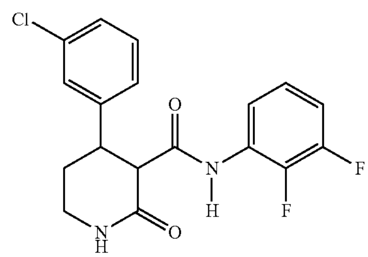 [SMILES: O=C1NCCC(c2cccc(Cl)c2)C1C(=O)Nc1cccc(F)c1F] |
| B911 | N-(2-fluorophenyl)-2-oxo-4-[3-(trifluoromethoxy)phenyl]piperidine-3-carboxamide | 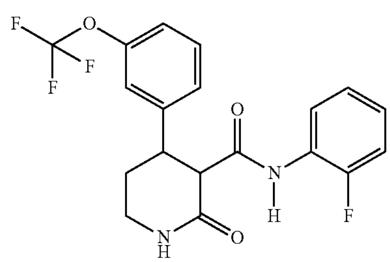 [SMILES: O=C1NCCC(c2cccc(OC(F)(F)F)c2)C1C(=O)Nc1ccccc1F] |
| B912 | 2-oxo-4-[3-(trifluoromethoxy)phenyl]-N-[2-(trifluoromethyl)phenyl]piperidine-3-carboxamide | 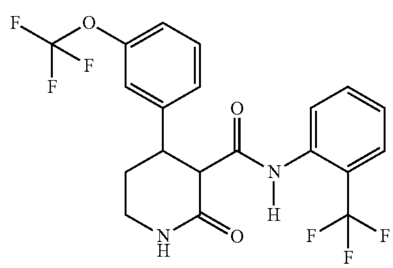 [SMILES: O=C1NCCC(c2cccc(OC(F)(F)F)c2)C1C(=O)Nc1ccccc1C(F)(F)F] |
| B913 | N-(2,3-difluorophenyl)-2-oxo-4-[3-(trifluoromethoxy)phenyl]piperidine-3-carboxamide | 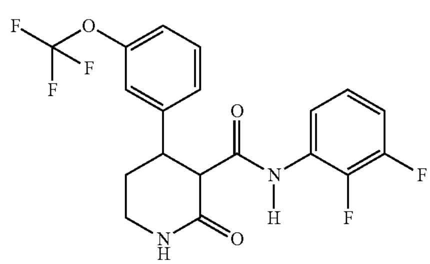 [SMILES: O=C1NCCC(c2cccc(OC(F)(F)F)c2)C1C(=O)Nc1cccc(F)c1F] |

TABLE B9-continued

Compound of formula B9 for use in compositions described herein (unless otherwise stated, all compounds are in racemic form).

| Compound | Name | Structure |
|---|---|---|
| B914 | (3R,4S)-4-(3-chlorophenyl)-N-(2,3-difluorophenyl)-2-oxo-piperidine-3-carboxamide | 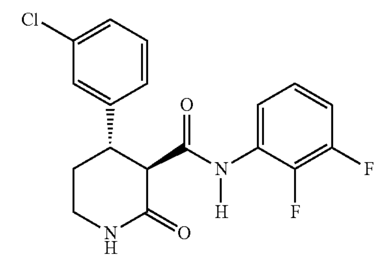 [SMILES: O=C1NCC[C@H](c2cccc(Cl)c2)[C@H]1C(=O)Nc1cccc(F)c1F] |
| B915 | 4-[3-(difluoromethyl)phenyl]-2-oxo-N-(2,3,4-trifluorophenyl)piperidine-3-carboxamide | 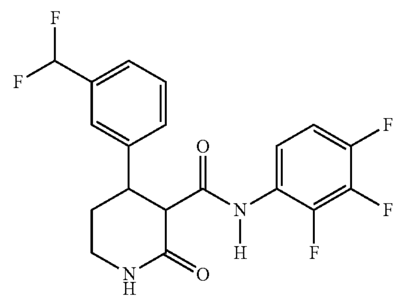 [SMILES: O=C1NCCC(c2cccc(C(F)F)c2)C1C(=O)Nc1ccc(F)c(F)c1F] |
| B916 | 4-[3-(difluoromethyl)phenyl]-N-(2-fluorophenyl)-2-oxo-piperidine-3-carboxamide | 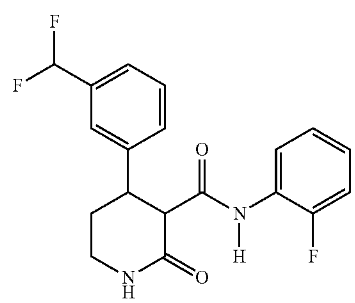 [SMILES: O=C1NCCC(c2cccc(C(F)F)c2)C1C(=O)Nc1ccccc1F] |
| B917 | 4-[3-(difluoromethyl)phenyl]-N-(2,3-difluorophenyl)-2-oxo-piperidine-3-carboxamide | 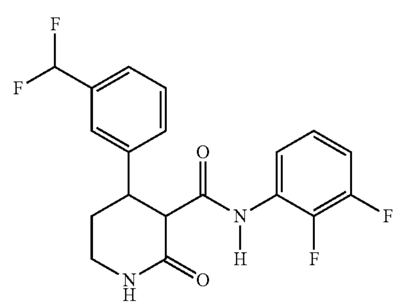 [SMILES: O=C1NCCC(c2cccc(C(F)F)c2)C1C(=O)Nc1cccc(F)c1F] |
| B918 | (3R,4S)-N-(2,3-difluorophenyl)-4-(4-fluorophenyl)-1-methyl-2-oxo-piperidine-3-carboxamide | 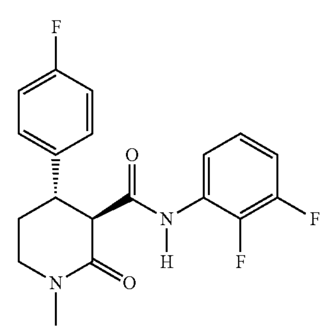 [SMILES: CN1CC[C@H](c2ccc(F)cc2)[C@@H](C(=O)Nc2cccc(F)c2F)C1=O] |

TABLE B9-continued

Compound of formula B9 for use in compositions described herein (unless otherwise stated, all compounds are in racemic form).

| Compound | Name | Structure |
|---|---|---|
| B919 | (3R,4S)-4-(4-fluorophenyl)-2-oxo-N-[2-(trifluoromethyl)phenyl]piperidine-3-carboxamide | 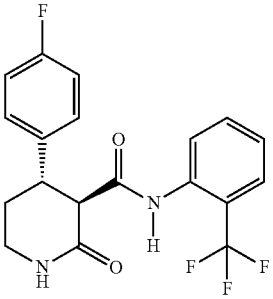 [SMILES: O=C1NCC[C@H](c2ccc(F)cc2)[C@H]1C(=O)Nc1ccccc1C(F)(F)F] |

Compounds of formula B9 as described herein may be made as described in WO2016/003997.

In one embodiment, with reference to the compositions referred to above, component (A) is compound 1.1. In another embodiment, with reference to the compositions referred to above, component (A) is compound 1.2. In another embodiment, with reference to the compositions referred to above, component (A) is compound 1.3. In another embodiment, with reference to the compositions referred to above, component (A) is compound 1.4. In another embodiment, with reference to the compositions referred to above, component (A) is compound 1.5. In another embodiment, with reference to the compositions referred to above, component (A) is compound 1.6. In another embodiment, with reference to the compositions referred to above, component (A) is compound 1.7. In another embodiment, with reference to the compositions referred to above, component (A) is compound 1.8. In another embodiment, with reference to the compositions referred to above, component (A) is compound 1.9. In another embodiment, with reference to the compositions referred to above, component (A) is compound 1.10. In another embodiment, with reference to the compositions referred to above, component (A) is compound 1.11. In another embodiment, with reference to the compositions referred to above, component (A) is compound 1.12. In another embodiment, with reference to the compositions referred to above, component (A) is compound 1.13. In another embodiment, with reference to the compositions referred to above, component (A) is compound 1.14.

Further example compositions of the invention comprise: Compound 1.1+acetochlor, compound 1.1+aciflurofen-sodium, compound 1.1+aclonifen, compound 1.1+alachlor, compound 1.1+alloxydim, compound 1.1+ametryn, compound 1.1+amicarbazone, compound 1.1+amidosulfuron, compound 1.1+aminocyclopyrachlor, compound 1.1+aminopyralid, compound 1.1+amitrole, compound 1.1+asulam, compound 1.1+atrazine, compound 1.1+beflubutamid, compound 1.1+benfluralin, compound 1.1+bensulfuron-methyl, compound 1.1+bentazone, compound 1.1+bicyclopyrone, compound 1.1+bifenox, compound 1.1+bispyribac-sodium, compound 1.1+bromacil, compound 1.1+bromoxynil, compound 1.1+butachlor, compound 1.1+butroxydim, compound 1.1+butafenacil, compound 1.1+cafenstrole, compound 1.1+carfentrazone-ethyl, compound 1.1+chloransulam, compound 1.1+chlorimuron-ethyl, compound 1.1+chlorotoluron, compound 1.1+chlorsulfuron, compound 1.1+cinosulfuron, compound 1.1+cinidon-ethyl, compound 1.1+clethodim, compound 1.1+clodinafop-propargyl, compound 1.1+clomazone, compound 1.1+clopyralid, compound 1.1+cycloxydim, compound 1.1+cyhalofop-butyl, compound 1.1+2,4-D (including the choline salt and 2-ethylhexyl ester thereof), compound 1.1+daimuron, compound 1.1+desmedipham, compound 1.1+dicamba (including the aluminium, aminopropyl, bis-aminopropylmethyl, choline, diglycolamine, dimethylamine, dimethylammonium, potassium and sodium salts thereof), compound 1.1+diclofop-methyl, compound 1.1+diclosulam, compound 1.1+difenzoquat, compound 1.1+diflufenican, compound 1.1+diflufenzopyr, compound 1.1+dimethachlor, compound 1.1+dimethenamid-P, compound 1.1+diquat dibromide, compound 1.1+diuron, compound 1.1+esprocarb, compound 1.1+ethametsulfuron, compound 1.1+ethofumesate, compound 1.1+fenoxaprop-P-ethyl, compound 1.1+fenquinotrione, compound 1.1+fentrazamide, compound 1.1+flazasulfuron, compound 1.1+florasulam, compound 1.1+fluazifop-P-butyl, compound 1.1+flucarbazone-sodium, compound 1.1+flufenacet, compound 1.1+flumetralin, compound 1.1+flumetsulam, compound 1.1+flumioxazin, compound 1.1+flupyrsulfuron-methyl-sodium, compound 1.1+fluroxypyr-meptyl, compound 1.1+flurtamone, compound 1.1+fluthiacet-methyl, compound 1.1+fomesafen, compound 1.1+foramsulfuron, compound 1.1+glufosinate (including the ammonium salt thereof), compound 1.1+glyphosate (including the diammonium, isopropylammonium and potassium salts thereof), compound 1.1+halauxifen-methyl, compound 1.1+halosulfuron-methyl, compound 1.1+haloxyfop-methyl, compound 1.1+hexazinone, compound 1.1+imazamethabenz, compound 1.1+imazamox, compound 1.1+imazapic, compound 1.1+imazapyr, compound 1.1+imazaquin, compound 1.1+imazethapyr, compound 1.1+indaziflam, compound 1.1+iodosulfuron-methyl-sodium, compound 1.1+iofensulfuron, compound 1.1+iofensulfuron-sodium, compound 1.1+ioxynil, compound 1.1+ipfencarbazone, compound 1.1+isoproturon, compound 1.1+isoxaben, compound 1.1+isoxaflutole, compound 1.1+lactofen, compound 1.1+linuron, compound 1.1+MCPA, compound 1.1+mecoprop-P, compound 1.1+mefenacet, compound 1.1+mesosulfuron, compound 1.1+mesosulfuron-methyl, compound 1.1+mesotrione, compound 1.1+metamitron, compound 1.1+metazachlor, compound 1.1+metobromuron, compound 1.1+metolachlor, compound 1.1+metoxuron, compound 1.1+metribuzin, compound 1.1+metsulfuron, compound 1.1+molinate, compound 1.1+ napropamide, compound 1.1+nicosulfuron, compound 1.1+ norflurazon, compound 1.1+orthosulfamuron, compound 1.1+oxadiargyl, compound 1.1+oxadiazon, compound 1.1+ oxasulfuron, compound 1.1+oxaziclomefone, compound 1.1+oxyfluorfen, compound 1.1+paraquat dichloride, compound 1.1+pendimethalin, compound 1.1+penoxsulam, compound 1.1+pethoxamid, compound 1.1+phenmedipham, compound 1.1+picloram, compound 1.1+picolinafen, compound 1.1+pinoxaden, compound 1.1+pretilachlor, compound 1.1+primisulfuron-methyl, compound 1.1+prodiamine, compound 1.1+prometryn, compound 1.1+ propachlor, compound 1.1+propanil, compound 1.1+propaquizafop, compound 1.1+propham, compound 1.1+ propoxycarbazone, compound 1.1+propyzamide, compound 1.1+prosulfocarb, compound 1.1+prosulfuron, compound 1.1+pyrasulfotole, compound 1.1+pyrazolynate, compound 1.1+pyrazosulfuron-ethyl, compound 1.1+pyribenzoxim, compound 1.1+pyridate, compound 1.1+pyriftalid, compound 1.1+pyrithiobac-sodium, compound 1.1+pyroxasulfone, compound 1.1+pyroxsulam, compound 1.1+quinclorac, compound 1.1+quizalofop-P-ethyl, compound 1.1+ rimsulfuron, compound 1.1+saflufenacil, compound 1.1+ sethoxydim, compound 1.1+S-metolachlor, compound 1.1+ sulcotrione, compound 1.1+sulfentrazone, compound 1.1+ sulfometuron-methyl, compound 1.1+sulfosulfuron, compound 1.1+tebuthiuron, compound 1.1+tefuryltrione, compound 1.1+tembotrione, compound 1.1+terbuthylazine, compound 1.1+terbutryn, compound 1.1+thiencarbazone, compound 1.1+thifensulfuron, compound 1.1+tiafenacil, compound 1.1+tolpyralate, compound 1.1+topramezone, compound 1.1+tralkoxydim, compound 1.1+triafamone, compound 1.1+triallate, compound 1.1+triasulfuron, compound 1.1+tribenuron-methyl, compound 1.1+triclopyr, compound 1.1+trifloxysulfuron-sodium, compound 1.1+trifludimoxazin, compound 1.1+trifluralin, compound 1.1+tritosulfuron and compound 1.1+4-amino-3-chloro-6-(4-chloro-2-fluoro-3-methoxyphenyl)-5-fluoropyridine-2-carboxylate (Compound B1), 1.1+4-hydroxy-1-methoxy-5-methyl-3-[4-(trifluoromethyl)-2-pyridyl]imidazolidin-2-one (Compound B2), 1.1+4-hydroxy-1,5-dimethyl-3-[4-(trifluoromethyl)-2-pyridyl]imidazolidin-2-one (Compound B3), 1.1+5-ethoxy-4-hydroxy-1-methyl-3-[4-(trifluoromethyl)-2-pyridyl]imidazolidin-2-one (Compound B4), 1.1+4-hydroxy-1-methyl-3-[4-(trifluoromethyl)-2-pyridyl]imidazolidin-2-one (Compound B5), 1.1+4-hydroxy-1,5-dimethyl-3-[1-methyl-5-(trifluoromethyl)pyrazol-3-yl]imidazolidin-2-one (Compound B6), 1.1+(4R) 1-(5-tert-butylisoxazol-3-yl)-4-ethoxy-5-hydroxy-3-methyl-imidazolidin-2-one (Compound B7);

compound 1.1+N-(2-fluorophenyl)-2-oxo-4-[3-(trifluoromethyl)phenyl]-pyrrolidine-3-carboxamide (compound B801), compound 1.1+N-(2,3-difluorophenyl)-2-oxo-4-[3-(trifluoromethyl)phenyl]pyrrolidine-3-carboxamide (compound B802), compound 1.1+2-oxo-4-[3-(trifluoromethyl)phenyl]-N-(2,3,4-trifluorophenyl)pyrrolidine-3-carboxamide (compound B803), compound 1.1+N-(2-fluorophenyl)-1-methyl-2-oxo-4-[3-(trifluoromethyl)phenyl]pyrrolidine-3-carboxamide (compound B804), compound 1.1+N-(2-fluorophenyl)-2-oxo-4-[4-(trifluoromethyl)phenyl]pyrrolidine-3-carboxamide (compound B805), compound 1.1+N-(2-fluorophenyl)-1-methyl-2-oxo-4-[4-(trifluoromethyl)phenyl]pyrrolidine-3-carboxamide (compound B806), compound 1.1+N-(2,3-difluorophenyl)-2-oxo-4-[4-(trifluoromethyl)phenyl]pyrrolidine-3-carboxamide (compound B807), compound 1.1+N-(2,3-difluorophenyl)-1-methyl-2-oxo-4-[4-(trifluoromethyl)phenyl]pyrrolidine-3-carboxamide (compound B808), compound 1.1+2-oxo-4-[4-(trifluoromethyl)phenyl]-N-(2,3,4-trifluorophenyl)pyrrolidine-3-carboxamide (compound B809), compound 1.1+N-(2-fluorophenyl)-4-(4-fluorophenyl)-1-methyl-2-oxo-pyrrolidine-3-carboxamide (compound B810), compound 1.1+N-(2,3-difluorophenyl)-4-(3,4-difluorophenyl)-2-oxo-pyrrolidine-3-carboxamide (compound B811), compound 1.1+4-(3,4-difluorophenyl)-N-(2-fluorophenyl)-2-oxo-pyrrolidine-3-carboxamide (compound B812), compound 1.1+N-(2,4-difluorophenyl)-4-(3,5-difluorophenyl)-2-oxo-pyrrolidine-3-carboxamide (compound B813), compound 1.1+N-(2,3-difluorophenyl)-4-(3-isopropylphenyl)-2-oxo-pyrrolidine-3-carboxamide (compound B814), compound 1.1+N-(2,3-difluorophenyl)-2-oxo-4-[6-(trifluoromethyl)-3-pyridyl]pyrrolidine-3-carboxamide (compound B815);

compound 1.1+4-(3,4-difluorophenyl)-2-oxo-N-[2-(trifluoromethyl)phenyl]-piperidine-3-carboxamide (compound B901), compound 1.1+N-(2,3-difluorophenyl)-2-oxo-4-[3-(trifluoromethyl)phenyl]piperidine-3-carboxamide (compound B902), compound 1.1+2-oxo-N-[2-(trifluoromethyl)phenyl]-4-[3-(trifluoromethyl)phenyl]piperidine-3-carboxamide (compound B903), compound 1.1+N-(2-chlorophenyl)-2-oxo-4-[4-(trifluoromethyl)phenyl]piperidine-3-carboxamide (compound B904), compound 1.1+N-(2-fluorophenyl)-2-oxo-4-[4-(trifluoromethyl)phenyl]piperidine-3-carboxamide (compound B905), compound 1.1+(3R,4S)—N-(2,3-difluorophenyl)-2-oxo-4-[3-(trifluoromethyl)phenyl]piperidine-3-carboxamide (compound B906), compound 1.1+(3R,4S)—N-(2,3-difluorophenyl)-2-oxo-4-[4-(trifluoromethyl)phenyl]piperidine-3-carboxamide (compound B907), compound 1.1+(3R,4S)—N-(3-chloro-2-fluoro-phenyl)-2-oxo-4-[3-(trifluoromethyl)phenyl]piperidine-3-carboxamide (compound B908), compound 1.1+(3R,4S)-2-oxo-4-[3-(trifluoromethyl)phenyl]-N-(2,3,4-trifluorophenyl) piperidine-3-carboxamide (compound 909), compound 1.1+N-(2,3-difluorophenyl)-2-oxo-4-phenyl-piperidine-3-carboxamide (compound B910), compound 1.1+N-(2-fluorophenyl)-2-oxo-4-[3-(trifluoromethoxy)phenyl]piperidine-3-carboxamide (compound B911), compound 1.1+2-oxo-4-[3-(trifluoromethoxy)phenyl]-N-[2-(trifluoromethyl)phenyl]piperidine-3-carboxamide (compound B912), compound 1.1+N-(2,3-difluorophenyl)-2-oxo-4-[3-(trifluoromethoxy)phenyl]piperidine-3-carboxamide (compound B913), compound 1.1+(3R,4S)-4-(3-chlorophenyl)-N-(2,3-difluorophenyl)-2-oxo-piperidine-3-carboxamide (compound B914), compound 1.1+4-[3-(difluoromethyl)phenyl]-2-oxo-N-(2,3,4-trifluorophenyl) piperidine-3-carboxamide (compound B915), compound 1.1+4-[3-(difluoromethyl)phenyl]-N-(2-fluorophenyl)-2-oxo-piperidine-3-carboxamide (compound B916), compound 1.1+4-[3-(difluoromethyl)phenyl]-N-(2,3-difluorophenyl)-2-oxo-piperidine-3-carboxamide (compound B917), compound 1.1+(3R,4S)—N-(2,3-difluorophenyl)-4-(4-fluorophenyl)-2-oxo-piperidine-3-carboxamide (compound B918), and compound 1.1+(3R,4S)-4-(4-fluorophenyl)-2-oxo-N-[2-(trifluoromethyl)phenyl]piperidine-3-carboxamide (compound B919).

In another embodiment, with reference to the compositions referred to above, component compound 1.1 is replaced by compound 1.2. In another embodiment, with reference to the compositions referred to above, component compound 1.1 is replaced by compound 1.3. In another embodiment, with reference to the compositions referred to above, component compound 1.1 is replaced by compound 1.4. In another embodiment, with reference to the compositions referred to above, component compound 1.1 is replaced by compound 1.5. In another embodiment, with reference to the compositions referred to above, component compound 1.1 is replaced by compound 1.6. In another embodiment, with reference to the compositions referred to above, component compound 1.1 is replaced by compound 1.7. In another embodiment, with reference to the compositions referred to above, component compound 1.1 is replaced by compound 1.8. In another embodiment, with reference to the compositions referred to above, component compound 1.1 is replaced by compound 1.9. In another embodiment, with reference to the compositions referred to above, component compound 1.1 is replaced by compound 1.10. In another embodiment, with reference to the compositions referred to above, component compound 1.1 is replaced by compound 1.11. In another embodiment, with reference to the compositions referred to above, component compound 1.1 is replaced by compound 1.12. In another embodiment, with reference to the compositions referred to above, component compound 1.1 is replaced by compound 1.13. In another embodiment, with reference to the compositions referred to above, component compound 1.1 is replaced by compound 1.14.

The mixing ratio of the compound of Formula (I) to the mixing partner B can vary depending on the nature of the mixing partner(s). Typical ratios include, for example, from 1:100 to 1000:1, from 1:50 to 50:1, or from 1:10 to 10:1.

Whilst two-way mixtures of a compound of formula (I) and another herbicide are explicitly disclosed above, the skilled man will appreciate that the invention extends to three-way and further multiple combinations comprising the above two-way mixtures. In particular, the present invention provides compositions comprising the three-way mixtures listed in Table 1 below (CMP=compound: see Table C1):

TABLE 1

| CMP | Mix Partner 1 | Mix Partner 2 | CMP | Mix Partner 1 | Mix Partner 2 |
|---|---|---|---|---|---|
| 1.1 | acetochlor | ametryn | 1.1 | flufenacet | 2,4 D |
| 1.1 | acetochlor | amicarbazone | 1.1 | flufenacet | amidosulfuron |
| 1.1 | acetochlor | atrazine | 1.1 | flufenacet | bicyclopyrone |
| 1.1 | acetochlor | bicyclopyrone | 1.1 | flufenacet | bromoxynil |
| 1.1 | acetochlor | bromoxynil | 1.1 | flufenacet | dicamba |
| 1.1 | acetochlor | clopyralid | 1.1 | flufenacet | diflufenican |
| 1.1 | acetochlor | 2,4 D | 1.1 | flufenacet | florasulam |
| 1.1 | acetochlor | dicamba | 1.1 | flufenacet | fluroxypy |
| 1.1 | acetochlor | dimethenamid-P | 1.1 | flufenacet | halauxifen |
| 1.1 | acetochlor | fenquinotrione | 1.1 | flufenacet | MCPA |
| 1.1 | acetochlor | foramsulfuron | 1.1 | flufenacet | metsulfuron |
| 1.1 | acetochlor | glufosinate | 1.1 | flufenacet | propoxycarbazone |
| 1.1 | acetochlor | glyphosate | 1.1 | flufenacet | prosulfuron |
| 1.1 | acetochlor | isoxaflutole | 1.1 | flufenacet | pyroxsulam |
| 1.1 | acetochlor | mesotrione | 1.1 | flufenacet | terbutryn |
| 1.1 | acetochlor | metribuzin | 1.1 | flufenacet | triasulfuron |
| 1.1 | acetochlor | nicosulfuron | 1.1 | foramsulfuron | glufosinate |
| 1.1 | acetochlor | pethoxamid | 1.1 | foramsulfuron | glyphosate |
| 1.1 | acetochlor | prosulfuron | 1.1 | foramsulfuron | isoxaflutole |
| 1.1 | acetochlor | pyridate | 1.1 | foramsulfuron | mesotrione |
| 1.1 | acetochlor | pyroxasulfone | 1.1 | foramsulfuron | metribuzin |
| 1.1 | acetochlor | rimsulfuron | 1.1 | foramsulfuron | nicosulfuron |
| 1.1 | acetochlor | S-metolachor | 1.1 | foramsulfuron | pethoxamid |
| 1.1 | acetochlor | sulcotrione | 1.1 | foramsulfuron | prosulfuron |
| 1.1 | acetochlor | tembotrione | 1.1 | foramsulfuron | pyridate |
| 1.1 | acetochlor | terbuthylazine | 1.1 | foramsulfuron | pyroxasulfone |
| 1.1 | acetochlor | tolpyralate | 1.1 | foramsulfuron | rimsulfuron |
| 1.1 | ametryn | amicarbazone | 1.1 | foramsulfuron | S-metolachor |
| 1.1 | ametryn | atrazine | 1.1 | foramsulfuron | sulcotrione |
| 1.1 | ametryn | bicyclopyrone | 1.1 | foramsulfuron | tembotrione |
| 1.1 | ametryn | bromoxynil | 1.1 | foramsulfuron | terbuthylazine |
| 1.1 | ametryn | clopyralid | 1.1 | foramsulfuron | tolpyralate |
| 1.1 | ametryn | 2,4 D | 1.1 | glufosinate | butafenacil |
| 1.1 | ametryn | dicamba | 1.1 | glufosinate | diuron |
| 1.1 | ametryn | dimethenamid-P | 1.1 | glufosinate | flazasulfuron |
| 1.1 | ametryn | fenquinotrione | 1.1 | glufosinate | Flumioxazin |
| 1.1 | ametryn | foramsulfuron | 1.1 | glufosinate | hexazinone |
| 1.1 | ametryn | glufosinate | 1.1 | glufosinate | glyphosate |
| 1.1 | ametryn | glyphosate | 1.1 | glufosinate | isoxaflutole |
| 1.1 | ametryn | isoxaflutole | 1.1 | glufosinate | mesotrione |
| 1.1 | ametryn | mesotrione | 1.1 | glufosinate | metribuzin |
| 1.1 | ametryn | metribuzin | 1.1 | glufosinate | metsulfuron |
| 1.1 | ametryn | nicosulfuron | 1.1 | glufosinate | nicosulfuron |
| 1.1 | ametryn | pethoxamid | 1.1 | glufosinate | norflurazon |
| 1.1 | ametryn | prosulfuron | 1.1 | glufosinate | oxadiazon |
| 1.1 | ametryn | pyridate | 1.1 | glufosinate | oxyflurofen |
| 1.1 | ametryn | pyroxasulfone | 1.1 | glufosinate | pethoxamid |
| 1.1 | ametryn | rimsulfuron | 1.1 | glufosinate | prometryn |
| 1.1 | ametryn | S-metolachor | 1.1 | glufosinate | prosulfuron |
| 1.1 | ametryn | sulcotrione | 1.1 | glufosinate | pyridate |
| 1.1 | ametryn | tembotrione | 1.1 | glufosinate | pyroxasulfone |
| 1.1 | ametryn | terbuthylazine | 1.1 | glufosinate | rimsulfuron |
| 1.1 | ametryn | tolpyralate | 1.1 | glufosinate | S-metolachor |
| 1.1 | amicarbazone | atrazine | 1.1 | glufosinate | saflufenacil |
| 1.1 | amicarbazone | bicyclopyrone | 1.1 | glufosinate | simazine |
| 1.1 | amicarbazone | bromoxynil | 1.1 | glufosinate | sulcotrione |
| 1.1 | amicarbazone | clopyralid | 1.1 | glufosinate | tembotrione |

TABLE 1-continued

| CMP | Mix Partner 1 | Mix Partner 2 | CMP | Mix Partner 1 | Mix Partner 2 |
|---|---|---|---|---|---|
| 1.1 | amicarbazone | 2,4 D | 1.1 | glufosinate | terbuthylazine |
| 1.1 | amicarbazone | dicamba | 1.1 | glufosinate | terbutryn |
| 1.1 | amicarbazone | dimethenamid-P | 1.1 | glufosinate | tolpyralate |
| 1.1 | amicarbazone | fenquinotrione | 1.1 | glufosinate | trifloxysulfuron |
| 1.1 | amicarbazone | foramsulfuron | 1.1 | glyphosate | Ametryn |
| 1.1 | amicarbazone | glufosinate | 1.1 | glyphosate | butafenacil |
| 1.1 | amicarbazone | glyphosate | 1.1 | glyphosate | diuron |
| 1.1 | amicarbazone | isoxaflutole | 1.1 | glyphosate | flazasulfuron |
| 1.1 | amicarbazone | mesotrione | 1.1 | glyphosate | Flumioxazin |
| 1.1 | amicarbazone | metribuzin | 1.1 | glyphosate | hexazinone |
| 1.1 | amicarbazone | nicosulfuron | 1.1 | glyphosate | metsulfuron |
| 1.1 | amicarbazone | pethoxamid | 1.1 | glyphosate | isoxaflutole |
| 1.1 | amicarbazone | prosulfuron | 1.1 | glyphosate | mesotrione |
| 1.1 | amicarbazone | pyridate | 1.1 | glyphosate | metribuzin |
| 1.1 | amicarbazone | pyroxasulfone | 1.1 | glyphosate | nicosulfuron |
| 1.1 | amicarbazone | rimsulfuron | 1.1 | glyphosate | norflurazon |
| 1.1 | amicarbazone | S-metolachor | 1.1 | glyphosate | oxadiazon |
| 1.1 | amicarbazone | sulcotrione | 1.1 | glyphosate | oxyflurofen |
| 1.1 | amicarbazone | tembotrione | 1.1 | glyphosate | pethoxamid |
| 1.1 | amicarbazone | terbuthylazine | 1.1 | glyphosate | prometryn |
| 1.1 | amicarbazone | tolpyralate | 1.1 | glyphosate | prosulfuron |
| 1.1 | atrazine | bicyclopyrone | 1.1 | glyphosate | pyridate |
| 1.1 | atrazine | bromoxynil | 1.1 | glyphosate | pyroxasulfone |
| 1.1 | atrazine | clopyralid | 1.1 | glyphosate | rimsulfuron |
| 1.1 | atrazine | 2,4 D | 1.1 | glyphosate | S-metolachor |
| 1.1 | atrazine | dicamba | 1.1 | glyphosate | saflufenacil |
| 1.1 | atrazine | dimethenamid-P | 1.1 | glyphosate | simazine |
| 1.1 | atrazine | fenquinotrione | 1.1 | glyphosate | sulcotrione |
| 1.1 | atrazine | foramsulfuron | 1.1 | glyphosate | tembotrione |
| 1.1 | atrazine | glufosinate | 1.1 | glyphosate | terbuthylazine |
| 1.1 | atrazine | glyphosate | 1.1 | glyphosate | terbutryn |
| 1.1 | atrazine | isoxaflutole | 1.1 | glyphosate | tolpyralate |
| 1.1 | atrazine | mesotrione | 1.1 | glyphosate | trifloxysulfuron |
| 1.1 | atrazine | metribuzin | 1.1 | iodosulfuron | 2,4 D |
| 1.1 | atrazine | nicosulfuron | 1.1 | iodosulfuron | amidosulfuron |
| 1.1 | atrazine | pethoxamid | 1.1 | iodosulfuron | bicyclopyrone |
| 1.1 | atrazine | prosulfuron | 1.1 | iodosulfuron | bromoxynil |
| 1.1 | atrazine | pyridate | 1.1 | iodosulfuron | dicamba |
| 1.1 | atrazine | pyroxasulfone | 1.1 | iodosulfuron | diflufenican |
| 1.1 | atrazine | rimsulfuron | 1.1 | iodosulfuron | florasulam |
| 1.1 | atrazine | S-metolachor | 1.1 | iodosulfuron | fluroxypy |
| 1.1 | atrazine | sulcotrione | 1.1 | iodosulfuron | halauxifen |
| 1.1 | atrazine | tembotrione | 1.1 | iodosulfuron | MCPA |
| 1.1 | atrazine | terbuthylazine | 1.1 | iodosulfuron | metsulfuron |
| 1.1 | atrazine | tolpyralate | 1.1 | iodosulfuron | propoxycarbazone |
| 1.1 | bicyclopyrone | bromoxynil | 1.1 | iodosulfuron | prosulfuron |
| 1.1 | bicyclopyrone | clopyralid | 1.1 | iodosulfuron | pyroxsulam |
| 1.1 | bicyclopyrone | 2,4 D | 1.1 | iodosulfuron | terbutryn |
| 1.1 | bicyclopyrone | dicamba | 1.1 | iodosulfuron | triasulfuron |
| 1.1 | bicyclopyrone | dimethenamid-P | 1.1 | isoxaflutole | mesotrione |
| 1.1 | bicyclopyrone | fenquinotrione | 1.1 | isoxaflutole | metribuzin |
| 1.1 | bicyclopyrone | foramsulfuron | 1.1 | isoxaflutole | nicosulfuron |
| 1.1 | bicyclopyrone | glufosinate | 1.1 | isoxaflutole | pethoxamid |
| 1.1 | bicyclopyrone | glyphosate | 1.1 | isoxaflutole | prosulfuron |
| 1.1 | bicyclopyrone | isoxaflutole | 1.1 | isoxaflutole | pyridate |
| 1.1 | bicyclopyrone | mesotrione | 1.1 | isoxaflutole | pyroxasulfone |
| 1.1 | bicyclopyrone | metribuzin | 1.1 | isoxaflutole | rimsulfuron |
| 1.1 | bicyclopyrone | nicosulfuron | 1.1 | isoxaflutole | S-metolachor |
| 1.1 | bicyclopyrone | pethoxamid | 1.1 | isoxaflutole | sulcotrione |
| 1.1 | bicyclopyrone | prosulfuron | 1.1 | isoxaflutole | tembotrione |
| 1.1 | bicyclopyrone | pyridate | 1.1 | isoxaflutole | terbuthylazine |
| 1.1 | bicyclopyrone | pyroxasulfone | 1.1 | isoxaflutole | tolpyralate |
| 1.1 | bicyclopyrone | rimsulfuron | 1.1 | mesosulfuron | 2,4 D |
| 1.1 | bicyclopyrone | S-metolachor | 1.1 | mesosulfuron | amidosulfuron |
| 1.1 | bicyclopyrone | sulcotrione | 1.1 | mesosulfuron | bicyclopyrone |
| 1.1 | bicyclopyrone | tembotrione | 1.1 | mesosulfuron | bromoxynil |
| 1.1 | bicyclopyrone | terbuthylazine | 1.1 | mesosulfuron | dicamba |
| 1.1 | bicyclopyrone | tolpyralate | 1.1 | mesosulfuron | diflufenican |
| 1.1 | bromoxynil | clopyralid | 1.1 | mesosulfuron | florasulam |
| 1.1 | bromoxynil | 2,4 D | 1.1 | mesosulfuron | fluroxypy |
| 1.1 | bromoxynil | dicamba | 1.1 | mesosulfuron | halauxifen |
| 1.1 | bromoxynil | dimethenamid-P | 1.1 | mesosulfuron | MCPA |
| 1.1 | bromoxynil | fenquinotrione | 1.1 | mesosulfuron | metsulfuron |
| 1.1 | bromoxynil | foramsulfuron | 1.1 | mesosulfuron | propoxycarbazone |
| 1.1 | bromoxynil | glufosinate | 1.1 | mesosulfuron | prosulfuron |
| 1.1 | bromoxynil | glyphosate | 1.1 | mesosulfuron | pyroxsulam |
| 1.1 | bromoxynil | isoxaflutole | 1.1 | mesosulfuron | terbutryn |
| 1.1 | bromoxynil | mesotrione | 1.1 | mesosulfuron | triasulfuron |

TABLE 1-continued

| CMP | Mix Partner 1 | Mix Partner 2 | CMP | Mix Partner 1 | Mix Partner 2 |
|---|---|---|---|---|---|
| 1.1 | bromoxynil | metribuzin | 1.1 | mesotrione | metribuzin |
| 1.1 | bromoxynil | nicosulfuron | 1.1 | mesotrione | nicosulfuron |
| 1.1 | bromoxynil | pethoxamid | 1.1 | mesotrione | pethoxamid |
| 1.1 | bromoxynil | prosulfuron | 1.1 | mesotrione | prosulfuron |
| 1.1 | bromoxynil | pyridate | 1.1 | mesotrione | pyridate |
| 1.1 | bromoxynil | pyroxasulfone | 1.1 | mesotrione | pyroxasulfone |
| 1.1 | bromoxynil | rimsulfuron | 1.1 | mesotrione | rimsulfuron |
| 1.1 | bromoxynil | S-metolachor | 1.1 | mesotrione | S-metolachor |
| 1.1 | bromoxynil | sulcotrione | 1.1 | mesotrione | sulcotrione |
| 1.1 | bromoxynil | tembotrione | 1.1 | mesotrione | tembotrione |
| 1.1 | bromoxynil | terbuthylazine | 1.1 | mesotrione | terbuthylazine |
| 1.1 | bromoxynil | tolpyralate | 1.1 | mesotrione | tolpyralate |
| 1.1 | clodinafop | 2,4 D | 1.1 | metribuzin | nicosulfuron |
| 1.1 | clodinafop | amidosulfuron | 1.1 | metribuzin | pethoxamid |
| 1.1 | clodinafop | bicyclopyrone | 1.1 | metribuzin | prosulfuron |
| 1.1 | clodinafop | bromoxynil | 1.1 | metribuzin | pyridate |
| 1.1 | clodinafop | dicamba | 1.1 | metribuzin | pyroxasulfone |
| 1.1 | clodinafop | diflufenican | 1.1 | metribuzin | rimsulfuron |
| 1.1 | clodinafop | florasulam | 1.1 | metribuzin | S-metolachor |
| 1.1 | clodinafop | fluroxypy | 1.1 | metribuzin | sulcotrione |
| 1.1 | clodinafop | halauxifen | 1.1 | metribuzin | tembotrione |
| 1.1 | clodinafop | MCPA | 1.1 | metribuzin | terbuthylazine |
| 1.1 | clodinafop | metsulfuron | 1.1 | metribuzin | tolpyralate |
| 1.1 | clodinafop | propoxycarbazone | 1.1 | nicosulfuron | pethoxamid |
| 1.1 | clodinafop | prosulfuron | 1.1 | nicosulfuron | prosulfuron |
| 1.1 | clodinafop | pyroxsulam | 1.1 | nicosulfuron | pyridate |
| 1.1 | clodinafop | terbutryn | 1.1 | nicosulfuron | pyroxasulfone |
| 1.1 | clodinafop | triasulfuron | 1.1 | nicosulfuron | rimsulfuron |
| 1.1 | clopyralid | 2,4 D | 1.1 | nicosulfuron | S-metolachor |
| 1.1 | clopyralid | dicamba | 1.1 | nicosulfuron | sulcotrione |
| 1.1 | clopyralid | dimethenamid-P | 1.1 | nicosulfuron | tembotrione |
| 1.1 | clopyralid | fenquinotrione | 1.1 | nicosulfuron | terbuthylazine |
| 1.1 | clopyralid | foramsulfuron | 1.1 | nicosulfuron | tolpyralate |
| 1.1 | clopyralid | glufosinate | 1.1 | paraquat | ametryn |
| 1.1 | clopyralid | glyphosate | 1.1 | paraquat | atrazine |
| 1.1 | clopyralid | isoxaflutole | 1.1 | paraquat | bicyclopyrone |
| 1.1 | clopyralid | mesotrione | 1.1 | paraquat | Butafenacil |
| 1.1 | clopyralid | metribuzin | 1.1 | paraquat | dicamba |
| 1.1 | clopyralid | nicosulfuron | 1.1 | paraquat | diuron |
| 1.1 | clopyralid | pethoxamid | 1.1 | paraquat | flazasulfuron |
| 1.1 | clopyralid | prosulfuron | 1.1 | paraquat | flumioxazin |
| 1.1 | clopyralid | pyridate | 1.1 | paraquat | hexazinon |
| 1.1 | clopyralid | pyroxasulfone | 1.1 | paraquat | mesotrione |
| 1.1 | clopyralid | rimsulfuron | 1.1 | paraquat | metribuzin |
| 1.1 | clopyralid | S-metolachor | 1.1 | paraquat | metsulfuron |
| 1.1 | clopyralid | sulcotrione | 1.1 | paraquat | norflurazon |
| 1.1 | clopyralid | tembotrione | 1.1 | paraquat | oxadiazon |
| 1.1 | clopyralid | terbuthylazine | 1.1 | paraquat | oxyfluorfen |
| 1.1 | clopyralid | tolpyralate | 1.1 | paraquat | prometryn |
| 1.1 | 2,4 D | dicamba | 1.1 | paraquat | rimsulfuron |
| 1.1 | 2,4 D | dimethenamid-P | 1.1 | paraquat | saflufenacil |
| 1.1 | 2,4 D | fenquinotrione | 1.1 | paraquat | simazine |
| 1.1 | 2,4 D | foramsulfuron | 1.1 | paraquat | S-Metolachlor |
| 1.1 | 2,4 D | glufosinate | 1.1 | paraquat | terbuthylazine |
| 1.1 | 2,4 D | glyphosate | 1.1 | paraquat | terbutryn |
| 1.1 | 2,4 D | isoxaflutole | 1.1 | paraquat | trifloxysulfuron |
| 1.1 | 2,4 D | mesotrione | 1.1 | pethoxamid | prosulfuron |
| 1.1 | 2,4 D | metribuzin | 1.1 | pethoxamid | pyridate |
| 1.1 | 2,4 D | nicosulfuron | 1.1 | pethoxamid | pyroxasulfone |
| 1.1 | 2,4 D | pethoxamid | 1.1 | pethoxamid | rimsulfuron |
| 1.1 | 2,4 D | prosulfuron | 1.1 | pethoxamid | S-metolachor |
| 1.1 | 2,4 D | pyridate | 1.1 | pethoxamid | sulcotrione |
| 1.1 | 2,4 D | pyroxasulfone | 1.1 | pethoxamid | tembotrione |
| 1.1 | 2,4 D | rimsulfuron | 1.1 | pethoxamid | terbuthylazine |
| 1.1 | 2,4 D | S-metolachor | 1.1 | pethoxamid | tolpyralate |
| 1.1 | 2,4 D | sulcotrione | 1.1 | pinoxaden | 2,4 D |
| 1.1 | 2,4 D | tembotrione | 1.1 | pinoxaden | amidosulfuron |
| 1.1 | 2,4 D | terbuthylazine | 1.1 | pinoxaden | bicyclopyrone |
| 1.1 | 2,4 D | tolpyralate | 1.1 | pinoxaden | bromoxynil |
| 1.1 | dicamba | dimethenamid-P | 1.1 | pinoxaden | dicamba |
| 1.1 | dicamba | fenquinotrione | 1.1 | pinoxaden | diflufenican |
| 1.1 | dicamba | foramsulfuron | 1.1 | pinoxaden | florasulam |
| 1.1 | dicamba | glufosinate | 1.1 | pinoxaden | fluroxypy |
| 1.1 | dicamba | glyphosate | 1.1 | pinoxaden | halauxifen |
| 1.1 | dicamba | isoxaflutole | 1.1 | pinoxaden | MCPA |
| 1.1 | dicamba | mesotrione | 1.1 | pinoxaden | metsulfuron |
| 1.1 | dicamba | metribuzin | 1.1 | pinoxaden | propoxycarbazone |
| 1.1 | dicamba | nicosulfuron | 1.1 | pinoxaden | prosulfuron |

TABLE 1-continued

| CMP | Mix Partner 1 | Mix Partner 2 | CMP | Mix Partner 1 | Mix Partner 2 |
|---|---|---|---|---|---|
| 1.1 | dicamba | pethoxamid | 1.1 | pinoxaden | pyroxsulam |
| 1.1 | dicamba | prosulfuron | 1.1 | pinoxaden | terbutryn |
| 1.1 | dicamba | pyridate | 1.1 | pinoxaden | triasulfuron |
| 1.1 | dicamba | pyroxasulfone | 1.1 | prosulfocarb | 2,4 D |
| 1.1 | dicamba | rimsulfuron | 1.1 | prosulfocarb | amidosulfuron |
| 1.1 | dicamba | S-metolachor | 1.1 | prosulfocarb | bicyclopyrone |
| 1.1 | dicamba | sulcotrione | 1.1 | prosulfocarb | bromoxynil |
| 1.1 | dicamba | tembotrione | 1.1 | prosulfocarb | dicamba |
| 1.1 | dicamba | terbuthylazine | 1.1 | prosulfocarb | diflufenican |
| 1.1 | dicamba | tolpyralate | 1.1 | prosulfocarb | florasulam |
| 1.1 | diquat | ametryn | 1.1 | prosulfocarb | fluroxypy |
| 1.1 | diquat | atrazine | 1.1 | prosulfocarb | halauxifen |
| 1.1 | diquat | bicyclopyrone | 1.1 | prosulfocarb | MCPA |
| 1.1 | diquat | butafenacil | 1.1 | prosulfocarb | metsulfuron |
| 1.1 | diquat | dicamba | 1.1 | prosulfocarb | propoxycarbazone |
| 1.1 | diquat | diuron | 1.1 | prosulfocarb | prosulfuron |
| 1.1 | diquat | flazasulfuron | 1.1 | prosulfocarb | pyroxsulam |
| 1.1 | diquat | flumioxazin | 1.1 | prosulfocarb | terbutryn |
| 1.1 | diquat | hexazinon | 1.1 | prosulfocarb | triasulfuron |
| 1.1 | diquat | mesotrione | 1.1 | prosulfuron | pyridate |
| 1.1 | diquat | metribuzin | 1.1 | prosulfuron | pyroxasulfone |
| 1.1 | diquat | metsulfuron | 1.1 | prosulfuron | rimsulfuron |
| 1.1 | diquat | norflurazon | 1.1 | prosulfuron | S-metolachor |
| 1.1 | diquat | oxadiazon | 1.1 | prosulfuron | sulcotrione |
| 1.1 | diquat | oxyfluorfen | 1.1 | prosulfuron | tembotrione |
| 1.1 | diquat | prometryn | 1.1 | prosulfuron | terbuthylazine |
| 1.1 | diquat | rimsulfuron | 1.1 | prosulfuron | tolpyralate |
| 1.1 | diquat | saflufenacil | 1.1 | pyridate | pyroxasulfone |
| 1.1 | diquat | simazine | 1.1 | pyridate | rimsulfuron |
| 1.1 | diquat | S-Metolachlor | 1.1 | pyridate | S-metolachor |
| 1.1 | diquat | terbuthylazine | 1.1 | pyridate | sulcotrione |
| 1.1 | diquat | terbutryn | 1.1 | pyridate | tembotrione |
| 1.1 | diquat | trifloxysulfuron | 1.1 | pyridate | terbuthylazine |
| 1.1 | dimethenamid-P | fenquinotrione | 1.1 | pyridate | tolpyralate |
| 1.1 | dimethenamid-P | foramsulfuron | 1.1 | pyroxasulfone | amidosulfuron |
| 1.1 | dimethenamid-P | glufosinate | 1.1 | pyroxasulfone | diflufenican |
| 1.1 | dimethenamid-P | glyphosate | 1.1 | pyroxasulfone | florasulam |
| 1.1 | dimethenamid-P | isoxaflutole | 1.1 | pyroxasulfone | fluroxypy |
| 1.1 | dimethenamid-P | mesotrione | 1.1 | pyroxasulfone | halauxifen |
| 1.1 | dimethenamid-P | metribuzin | 1.1 | pyroxasulfone | MCPA |
| 1.1 | dimethenamid-P | nicosulfuron | 1.1 | pyroxasulfone | metsulfuron |
| 1.1 | dimethenamid-P | pethoxamid | 1.1 | pyroxasulfone | propoxycarbazone |
| 1.1 | dimethenamid-P | prosulfuron | 1.1 | pyroxasulfone | pyroxsulam |
| 1.1 | dimethenamid-P | pyridate | 1.1 | pyroxasulfone | rimsulfuron |
| 1.1 | dimethenamid-P | pyroxasulfone | 1.1 | pyroxasulfone | S-metolachor |
| 1.1 | dimethenamid-P | rimsulfuron | 1.1 | pyroxasulfone | sulcotrione |
| 1.1 | dimethenamid-P | S-metolachor | 1.1 | pyroxasulfone | tembotrione |
| 1.1 | dimethenamid-P | sulcotrione | 1.1 | pyroxasulfone | terbuthylazine |
| 1.1 | dimethenamid-P | tembotrione | 1.1 | pyroxasulfone | tolpyralate |
| 1.1 | dimethenamid-P | terbuthylazine | 1.1 | pyroxasulfone | terbutryn |
| 1.1 | dimethenamid-P | tolpyralate | 1.1 | pyroxasulfone | triasulfuron |
| 1.1 | fenoxaprop | 2,4 D | 1.1 | rimsulfuron | S-metolachor |
| 1.1 | fenoxaprop | amidosulfuron | 1.1 | rimsulfuron | sulcotrione |
| 1.1 | fenoxaprop | bicyclopyrone | 1.1 | rimsulfuron | tembotrione |
| 1.1 | fenoxaprop | bromoxynil | 1.1 | rimsulfuron | terbuthylazine |
| 1.1 | fenoxaprop | dicamba | 1.1 | rimsulfuron | tolpyralate |
| 1.1 | fenoxaprop | diflufenican | 1.1 | S-metolachor | amidosulfuron |
| 1.1 | fenoxaprop | florasulam | 1.1 | S-metolachor | diflufenican |
| 1.1 | fenoxaprop | fluroxypy | 1.1 | S-metolachor | florasulam |
| 1.1 | fenoxaprop | halauxifen | 1.1 | S-metolachor | fluroxypy |
| 1.1 | fenoxaprop | MCPA | 1.1 | S-metolachor | halauxifen |
| 1.1 | fenoxaprop | metsulfuron | 1.1 | S-metolachor | MCPA |
| 1.1 | fenoxaprop | propoxycarbazone | 1.1 | S-metolachor | metsulfuron |
| 1.1 | fenoxaprop | prosulfuron | 1.1 | S-metolachor | propoxycarbazone |
| 1.1 | fenoxaprop | pyroxsulam | 1.1 | S-metolachor | pyroxsulam |
| 1.1 | fenoxaprop | terbutryn | 1.1 | S-metolachor | sulcotrione |
| 1.1 | fenoxaprop | triasulfuron | 1.1 | S-metolachor | tembotrione |
| 1.1 | fenquinotrione | foramsulfuron | 1.1 | S-metolachor | terbuthylazine |
| 1.1 | fenquinotrione | glufosinate | 1.1 | S-metolachor | tolpyralate |
| 1.1 | fenquinotrione | glyphosate | 1.1 | S-metolachor | terbutryn |
| 1.1 | fenquinotrione | isoxaflutole | 1.1 | S-metolachor | triasulfuron |
| 1.1 | fenquinotrione | mesotrione | 1.1 | sulcotrione | tembotrione |
| 1.1 | fenquinotrione | metribuzin | 1.1 | sulcotrione | terbuthylazine |
| 1.1 | fenquinotrione | nicosulfuron | 1.1 | sulcotrione | tolpyralate |
| 1.1 | fenquinotrione | pethoxamid | 1.1 | tembotrione | terbuthylazine |
| 1.1 | fenquinotrione | prosulfuron | 1.1 | tembotrione | tolpyralate |
| 1.1 | fenquinotrione | pyridate | 1.1 | terbuthylazine | tolpyralate |
| 1.1 | fenquinotrione | pyroxasulfone | 1.1 | thiencarbazone | 2,4 D |

TABLE 1-continued

| CMP | Mix Partner 1 | Mix Partner 2 | CMP | Mix Partner 1 | Mix Partner 2 |
|---|---|---|---|---|---|
| 1.1 | fenquinotrione | rimsulfuron | 1.1 | thiencarbazone | amidosulfuron |
| 1.1 | fenquinotrione | S-metolachor | 1.1 | thiencarbazone | bicyclopyrone |
| 1.1 | fenquinotrione | sulcotrione | 1.1 | thiencarbazone | bromoxynil |
| 1.1 | fenquinotrione | tembotrione | 1.1 | thiencarbazone | dicamba |
| 1.1 | fenquinotrione | terbuthylazine | 1.1 | thiencarbazone | diflufenican |
| 1.1 | fenquinotrione | tolpyralate | 1.1 | thiencarbazone | florasulam |
| 1.1 | flucarbazone | 2,4 D | 1.1 | thiencarbazone | fluroxypy |
| 1.1 | flucarbazone | amidosulfuron | 1.1 | thiencarbazone | halauxifen |
| 1.1 | flucarbazone | bicyclopyrone | 1.1 | thiencarbazone | MCPA |
| 1.1 | flucarbazone | bromoxynil | 1.1 | thiencarbazone | metsulfuron |
| 1.1 | flucarbazone | dicamba | 1.1 | thiencarbazone | propoxycarbazone |
| 1.1 | flucarbazone | diflufenican | 1.1 | thiencarbazone | prosulfuron |
| 1.1 | flucarbazone | florasulam | 1.1 | thiencarbazone | pyroxsulam |
| 1.1 | flucarbazone | fluroxypy | 1.1 | thiencarbazone | terbutryn |
| 1.1 | flucarbazone | halauxifen | 1.1 | thiencarbazone | triasulfuron |
| 1.1 | flucarbazone | MCPA | | | |
| 1.1 | flucarbazone | metsulfuron | | | |
| 1.1 | flucarbazone | propoxycarbazone | | | |
| 1.1 | flucarbazone | prosulfuron | | | |
| 1.1 | flucarbazone | pyroxsulam | | | |
| 1.1 | flucarbazone | terbutryn | | | |
| 1.1 | flucarbazone | triasulfuron | | | |

The present invention further provides compositions as defined in Tables 2 to 14 below. PGPubs, publish as is.

TABLE 2. Compositions comprising the three-way mixtures listed in Table 1 above, wherein the compound 1.1 is replaced with compound 1.2 (see Table C1).

TABLE 3. Compositions comprising the three-way mixtures listed in Table 1 above, wherein the compound 1.1 is replaced with compound 1.3 (see Table C1).

TABLE 4. Compositions comprising the three-way mixtures listed in Table 1 above, wherein the compound 1.1 is replaced with compound 1.4 (see Table C1).

TABLE 5. Compounds comprising the three-way mixtures listed in Table 1 above, wherein the compound 1.1 is replaced with compound 1.5 (see Table C1).

TABLE 6. Compounds comprising the three-way mixtures listed in Table 1 above, wherein the compound 1.1 is replaced with compound 1.6 (see Table C1).

TABLE 7. Compounds comprising three-way mixtures listed in Table 1 above, wherein the compound 1.1 is replaced with compound 1.7 (see Table C1).

TABLE 8. Compounds comprising three-way mixtures listed in Table 1 above, wherein the compound 1.1 is replaced with compound 1.8 (see Table C1).

TABLE 9. Compounds comprising three-way mixtures listed in Table 1 above, wherein the compound 1.1 is replaced with compound 1.9 (see Table C1).

TABLE 10. Compounds comprising three-way mixtures listed in Table 1 above, wherein the compound 1.1 is replaced with compound 1.10 (see Table C1).

TABLE 11. Compounds comprising three-way mixtures listed in Table 1 above, wherein the compound 1.1 is replaced with compound 1.11 (see Table C1).

TABLE 12. Compounds comprising three-way mixtures listed in Table 1 above, wherein the compound 1.1 is replaced with compound 1.12 (see Table C1).

TABLE 13. Compounds comprising three-way mixtures listed in Table 1 above, wherein the compound 1.1 is replaced with compound 1.13 (see Table C1).

TABLE 14. Compounds comprising three-way mixtures listed in Table 1 above, wherein the compound 1.1 is replaced with compound 1.14 (see Table C1).

The compositions of the invention can further include one or more safeners. In particular, the following safeners are particularly preferred: AD 67 (MON 4660), benoxacor, cloquintocet-mexyl, cyometrinil, cyprosulfamide, dichlormid, dicyclonon, dietholate, fenchlorazole-ethyl, fenclorim, flurazole, fluxofenim, furilazole, furilazome, isoxadifen-ethyl, mefenpyr-diethyl, mephenate, oxabetrinil, naphthalic anhydride (CAS RN 81-84-5), TI-35, N-isopropyl-4-(2-methoxy-benzoylsulfamoyl)-benzamide (CAS RN 221668-34-4) and N-(2-methoxybenzoyl)-4-[(methylaminocarbonyl)amino]benzenesulfonamide. Preferably the mixing ratio of compound of Formula I to safener is from 100:1 to 1:10, especially from 20:1 to 1:1.

Particularly preferred safeners are cloquintocet-mexyl, cyprosulfamide, isoxadifen-ethyl, mefenpyr-diethyl and N-(2-methoxybenzoyl)-4-[(methylaminocarbonyl)amino]benzenesulfonamide.

Preferred compositions of the invention and safeners include:

Compound 1.1, atrazine and cloquintocet-mexyl; compound 1.1, atrazine and cyprosulfamide; compound 1.1, atrazine and isoxadifen-ethyl; compound 1.1, atrazine and mefenpyr-diethyl; compound 1.1, atrazine and N-(2-methoxybenzoyl)-4-[(methylaminocarbonyl)amino]benzenesulfonamide.

Compound 1.1, tebuthylazine and cloquintocet-mexyl; compound 1.1, tebuthylazine and cyprosulfamide; compound 1.1, tebuthylazine and isoxadifen-ethyl; compound 1.1, tebuthylazine and mefenpyr-diethyl; compound 1.1, tebuthylazine and N-(2-methoxybenzoyl)-4-[(methylaminocarbonyl)amino]benzenesulfonamide.

Compound 1.1, mesotrione and cloquintocet-mexyl; compound 1.1, mesotrione and cyprosulfamide; compound 1.1, mesotrione and isoxadifen-ethyl; compound 1.1, mesotrione and mefenpyr-diethyl; compound 1.1, mesotrione and N-(2-methoxybenzoyl)-4-[(methylaminocarbonyl)amino]benzenesulfonamide.

Compound 1.1, bicyclopyrone and cloquintocet-mexyl; compound 1.1, bicyclopyrone and cyprosulfamide; compound 1.1, bicyclopyrone and isoxadifen-ethyl; compound 1.1, bicyclopyrone and mefenpyr-diethyl; compound 1.1, bicyclopyrone and N-(2-methoxybenzoyl)-4-[(methylaminocarbonyl)amino]benzenesulfonamide.

Compound 1.1, nicosulfuron and cloquintocet-mexyl; compound 1.1, nicosulfuron and cyprosulfamide; compound 1.1, nicosulfuron and isoxadifen-ethyl; compound 1.1, nicosulfuron and mefenpyr-diethyl; compound 1.1, nicosulfuron and N-(2-methoxybenzoyl)-4-[(methylaminocarbonyl)amino]benzenesulfonamide.

Compound 1.1, S-metolachlor and cloquintocet-mexyl; compound 1.1, S-metolachlor and cyprosulfamide; compound 1.1, S-metolachlor and isoxadifen-ethyl; compound 1.1, S-metolachlor and mefenpyr-diethyl; compound 1.1, S-metolachlor and N-(2-methoxybenzoyl)-4-[(methylaminocarbonyl)amino]benzenesulfonamide.

Compound 1.1, bromoxynil and cloquintocet-mexyl, compound 1.1, bromoxynil and cyprosulfamide, compound 1.1, bromoxynil and isoxadifen-ethyl, compound 1.1, bromoxynil and mefenpyr-diethyl, compound 1.1, bromoxynil and N-(2-methoxybenzoyl)-4-[(methylaminocarbonyl)amino]benzenesulfonamide.

Compound 1.1, pinoxaden and cloquintocet-mexyl, compound 1.1, pinoxaden and cyprosulfamide, compound 1.1, pinoxaden and isoxadifen-ethyl, compound 1.1, pinoxaden and mefenpyr-diethyl, compound 1.1, pinoxaden and N-(2-methoxybenzoyl)-4-[(methylaminocarbonyl)amino]benzenesulfonamide.

Compound 1.1, clodinafop-propargyl and cloquintocet-mexyl, compound 1.1, clodinafop-propargyl and cyprosulfamide, compound 1.1 clodinafop-propargyl and isoxadifen-ethyl, compound 1.1, clodinafop-propargyl and mefenpyr-diethyl, compound 1.1, clodinafop-propargyl and N-(2-methoxybenzoyl)-4-[(methylaminocarbonyl)amino]benzenesulfonamide.

Compound 1.1, fenoxaprop-P-ethyl and cloquintocet-mexyl, compound 1.1, fenoxaprop-P-ethyl and cyprosulfamide, compound 1.1 fenoxaprop-P-ethyl and isoxadifen-ethyl, compound 1.1, fenoxaprop-P-ethyl and mefenpyr-diethyl, compound 1.1, fenoxaprop-P-ethyl and N-(2-methoxybenzoyl)-4-[(methylaminocarbonyl)amino-]benzenesulfonamide.

Compound 1.1, mesosulfuron and cloquintocet-mexyl, compound 1.1, mesosulfuron and cyprosulfamide, compound 1.1 mesosulfuron and isoxadifen-ethyl, compound 1.1, mesosulfuron and mefenpyr-diethyl, compound 1.1, mesosulfuron and N-(2-methoxybenzoyl)-4-[(methylaminocarbonyl)amino]benzenesulfonamide.

Compound 1.1, iodosulfuron-methyl-sodium and cloquintocet-mexyl, compound 1.1, iodosulfuron-methyl-sodium and cyprosulfamide, compound 1.1 iodosulfuron-methyl-sodium and isoxadifen-ethyl, compound 1.1, iodosulfuron-methyl-sodium and mefenpyr-diethyl, compound 1.1, iodosulfuron-methyl-sodium and N-(2-methoxybenzoyl)-4-[(methylaminocarbonyl)amino]benzenesulfonamide.

Compound 1.1, thiencarbazone and cloquintocet-mexyl, compound 1.1, thiencarbazone and cyprosulfamide, compound 1.1 thiencarbazone and isoxadifen-ethyl, compound 1.1, thiencarbazone and mefenpyr-diethyl, compound 1.1, thiencarbazone and N-(2-methoxybenzoyl)-4-[(methylaminocarbonyl)-amino]benzenesulfonamide.

Compound 1.1, compound B2 and cloquintocet-mexyl, compound 1.1, compound B2 and cyprosulfamide, compound 1.1 compound B2 and isoxadifen-ethyl, compound 1.1, compound B2 and mefenpyr-diethyl, compound 1.1, compound B2 and N-(2-methoxybenzoyl)-4-[(methylaminocarbonyl)amino]benzenesulfonamide.

Compound 1.1, compound B3 and cloquintocet-mexyl, compound 1.1, compound B3 and cyprosulfamide, compound 1.1 compound B3 and isoxadifen-ethyl, compound 1.1, compound B3 and mefenpyr-diethyl, compound 1.1, compound B3 and N-(2-methoxybenzoyl)-4-[(methylaminocarbonyl)amino]benzenesulfonamide.

Compound 1.1, compound B4 and cloquintocet-mexyl, compound 1.1, compound B4 and cyprosulfamide, compound 1.1 compound B2 and isoxadifen-ethyl, compound 1.1, compound B4 and mefenpyr-diethyl, compound 1.1, compound B4 and N-(2-methoxybenzoyl)-4-[(methylaminocarbonyl)amino]benzenesulfonamide.

Compound 1.1, compound B5 and cloquintocet-mexyl, compound 1.1, compound B5 and cyprosulfamide, compound 1.1 compound B5 and isoxadifen-ethyl, compound 1.1, compound B5 and mefenpyr-diethyl, compound 1.1, compound B5 and N-(2-methoxybenzoyl)-4-[(methylaminocarbonyl)amino]benzenesulfonamide.

Compound 1.1, compound B6 and cloquintocet-mexyl, compound 1.1, compound B6 and cyprosulfamide, compound 1.1 compound B6 and isoxadifen-ethyl, compound 1.1, compound B6 and mefenpyr-diethyl, compound 1.1, compound B6 and N-(2-methoxybenzoyl)-4-[(methylaminocarbonyl)amino]benzenesulfonamide.

Compound 1.1, compound B7 and cloquintocet-mexyl, compound 1.1, compound B7 and cyprosulfamide, compound 1.1 compound B7 and isoxadifen-ethyl, compound 1.1, compound B7 and mefenpyr-diethyl, compound 1.1, compound B7 and N-(2-methoxybenzoyl)-4-[(methylaminocarbonyl)amino]benzenesulfonamide.

Further preferred compositions of the invention and safeners include compositions defined above wherein Compound 1.1 is substituted with Compound 1.2.

Further preferred compositions of the invention and safeners include compositions defined above wherein Compound 1.1 is substituted with Compound 1.3. Further preferred compositions of the invention and safeners include compositions defined above wherein Compound 1.1 is substituted with Compound 1.4. Further preferred compositions of the invention and safeners include compositions defined above wherein Compound 1.1 is substituted with Compound 1.5. Further preferred compositions of the invention and safeners include compositions defined above wherein Compound 1.1 is substituted with Compound 1.6. Further preferred compositions of the invention and safeners include compositions defined above wherein Compound 1.1 is substituted with Compound 1.7. Further preferred compositions of the invention and safeners include compositions defined above wherein Compound 1.1 is substituted with Compound 1.8. Further preferred compositions of the invention and safeners include compositions defined above wherein Compound 1.1 is substituted with Compound 1.9. Further preferred compositions of the invention and safeners include compositions defined above wherein Compound 1.1 is substituted with Compound 1.10. Further preferred compositions of the invention and safeners include compositions defined above wherein Compound 1.1 is substituted with Compound 1.11. Further preferred compositions of the invention and safeners include compositions defined above wherein Compound 1.1 is substituted with Compound 1.12. Further preferred compositions of the invention and safeners include compositions defined above wherein Compound 1.1 is substituted with Compound 1.13. Further preferred compositions of the invention and safeners include compositions defined above wherein Compound 1.1 is substituted with Compound 1.14.

The compounds of Formula I can also be used in mixtures with other agrochemicals such as fungicides, nematicides or insecticides, examples of which are given in The Pesticide Manual, Sixteenth Edition, British Crop Protection Council, 2012.

The present invention still further provides a method of controlling weeds at a locus said method comprising application to the locus of a weed controlling amount of a composition comprising a compound of Formula (I). Moreover, the present invention further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow. The application may be applied to the locus pre-emergence and/or postemergence of the crop plant. Some crop plants may be inherently tolerant to herbicidal effects of compounds of Formula (I). Preferred crop plants include maize, wheat, barley and rice. However, in some instances tolerance may need to be engineered into the crop plant, for example by way of genetic engineering. Thus, it is possible that the crop plant is rendered tolerant to 4-hydroxyphenylpyruvate dioxygenase (HPPD)-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria*, *Cenchrus*, *Lolium*, *Festuca*, *Setaria*, *Eleusine*, *Sorghum* or *Avena* species. Several HPPD-tolerant soybean transgenic "events" are known, and include for example SYHT04R (WO2012/082542), SYHT0H2 (WO2012/082548) and FG72. Accordingly, the herbicidal compounds of the present invention have broad application in a number of crop plants, including cereals, for example barley and wheat, cotton, oilseed rape, sunflower, maize, rice, soybeans, sugar beet, sugar cane and turf. Crop plants can also include trees, such as fruit trees, palm trees, coconut trees or other nuts. Also included are vines such as grapes, fruit bushes, fruit plants and vegetables.

The rates of application of compounds of Formula I may vary within wide limits and depend on the nature of the soil, the method of application (pre- or postemergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 25 to 1000 g/ha, more especially from 25 to 250 g/ha.

The application is generally made by spraying the composition, typically by tractor mounted sprayer for large areas, but other methods such as dusting (for powders), drip or drench can also be used.

Crop plants are to be understood as also including those crop plants which have been rendered tolerant to other herbicides or classes of herbicides (e.g. ALS-, GS-, EPSPS-, PPO-, and ACCase-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crop plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta@. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*.

In a further aspect of the present invention there is provided the use of a compound of Formula (I) as defined herein as a herbicide.

The compounds of the present invention can be prepared according to the following schemes.

Preparation of compounds Formula (I) is carried out analogously to known processes and comprises reacting a compound of Formula (IIc):

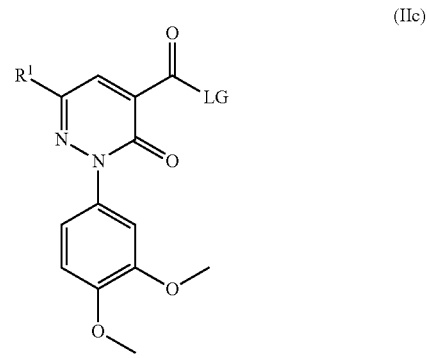

(IIc)

where the definition of $R^1$ is as for Formula (I) and LG is a suitable leaving group, for example a halogen atom, such as chlorine, or an alkoxy or aryloxy group, such as 4-nitrophenoxy, in an inert organic solvent, such as dichloromethane or acetonitrile, in the presence of a base, such as triethylamine, with a diketone of Formula (III)

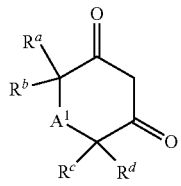

(III)

wherein
A¹ and $R^a$, $R^b$, $R^c$, $R^d$ are as defined previously in respect of Formula (I);
to give an ester of Formula (IV):—

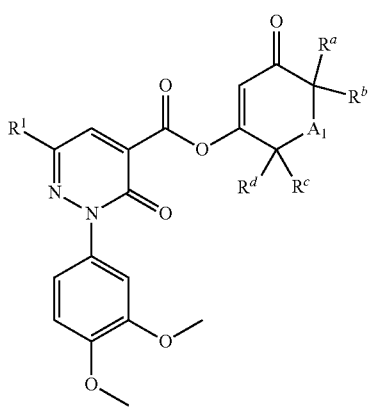

(IV)

which may be rearranged using catalysts, such as 4-dimethylaminopyridine, or acetone cyanohydrin, or a metal cyanide salt, such as sodium cyanide, in the presence of a suitable base, such as triethylamine, to give compounds of Formula (I).

Thus, according to a further aspect of the present invention there is provided a compound of Formula (II)

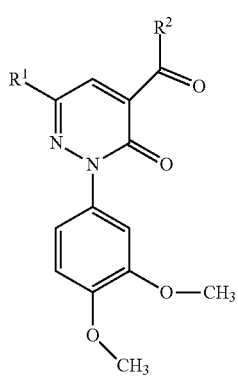

(II)

wherein
R¹ is as defined as before and R² is selected from the group consisting of halogen, —OH, $C_1$-$C_6$ alkoxy, aryloxy and N-linked imdazolyl. In this context, aryloxy is preferably a phenoxy group optionally substituted on the phenyl ring by one to five groups consisting of: fluoro, chloro, nitro, cyano, $C_1$-$C_3$alkyl, $C_1$-$C_3$alkoxy and $C_1$-$C_3$haloalkyl. Specific examples of preferred aryloxy groups thus include phenoxy, 4-nitrophenoxy and 2,3,4,5,6-pentafluorophenoxy.

TABLE C2

Examples of compounds of the present invention.

| Cmp | R¹ | R² | ¹H NMR (400 MHz, CDCl₃) |
|---|---|---|---|
| 2.1 | cPr | —Cl | |
| 2.2 | cPr | —OH | 14.10 (br. s, 1H), 8.06 (s, 1H), 7.14 (m, 1H), 7.10 (m, 1H), 6.97 (d, 1H), 3.95 (s, 3H), 3.90 (s, 3H), 2.10 (m, 1H), 1.15 (m, 2H), 1.00 (m, 2H). |
| 2.3 | cPr | —O—C₂H₅ | 7.55 (s, 1H), 7.11 (m, 2H), 6.91 (d, 1H), 4.40 (q, 2H), 3.94 (s, 3H), 3.90 (s, 3H), 1.97 (m, 1H), 1.40 (t, 3H), 1.04 (m, 2H), 0.92 (m, 2H). |
| 2.4 | CH₃ | —Cl | 7.88 (s, 1H), 7.14-7.11 (m, 2H), 6.94 (d, 1H), 3.93 (s, 3H), 3.90 (s, 3H), 2.51 (s, 3H) |
| 2.5 | CH₃ | —OH | 14.01 (br. s, 1H), 8.18 (s, 1H), 7.16 (d, 1H), 7.08 (br. s, 1H), 6.98 (d, 1H), 3.94 (app. d, 6H), 2.55 (s, 3H). |
| 2.6 | CH₃ | —O—C₂H₅ | 7.66 (s, 1H), 7.11 (br. s, 2H), 6.93 (d, 1H), 4.41 (q, 2H), 3.92 (s, 3H), 3.90 (s, 3H), 2.44 (s, 3H), 1.39 (t, 3H). |
| 2.7 | CH₃ | ![imidazolyl] | 8.07 (s, 1H), 7.58-7.53 (m, 2H), 7.49 (t, J = 1.5 Hz, 1H), 7.48 (s, 1H), 7.12 (dd, J = 0.6, 1.7 Hz, 1H), 7.01-6.97 (m, 2H), 3.85 (s, 3H), 2.50 (s, 3H) |
| 2.8 | cPr | ![imidazolyl] | |
| 2.9 | CH₃ | —O—CH₃ | |
| 2.10 | cPr | —O—CH₃ | |
| 2.11 | CH₃ | —O—tBu | |
| 2.12 | cPr | —O—tBu | |
| 2.13 | CH₃ | —O—iPr | |
| 2.14 | cPr | —O—iPr | |

The diketones of Formula (III) may be commercially available or, where they are not, prepared through methods detailed in the literature. For example, the preparation of the dione where A¹ is C=O and $R^a$, $R^b$, $R^c$ and $R^d$ are all methyl is detailed in *Tetrahedron* 2013, 8559-8563. The preparation of the dione where A¹ is CH(ethyl) and $R^a$, $R^b$, R and $R^d$ are all hydrogen is detailed in *Tetrahedron*, 2000, 4753-4758. The preparation of the dione where A¹ is CH₂, $R^a$-$R^c$ is —CH₂CH₂— and $R^b$ and $R^d$ are both hydrogen is detailed in *Tetrahedron Lett.* 2013, 557-561. The preparation of the dione where A¹ is CH₂ and $R^a$, $R^b$, $R^c$ and $R^d$ are all methyl is detailed in U.S. Pat. No. 5,006,150 A1, 1991.

Thus, according to a further aspect of the present invention, there is provided a method of producing a compound of Formula (I) comprising (i) reacting, in an inert organic solvent and in the presence of a base, a compound of Formula (IIc):

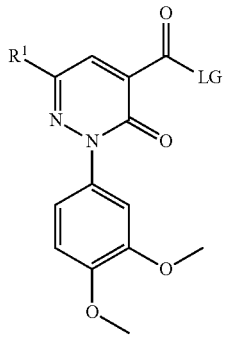

where the definition of $R^1$ is as for Formula (I) and LG is a suitable leaving group (for example a halogen atom, such as chlorine, or an alkoxy or aryloxy group, such as 4-nitrophenoxy), with a diketone of Formula (III)

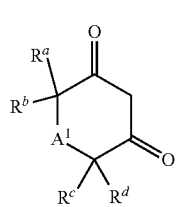

and (ii) rearrangement of the resulting product into the compound of Formula (I).

Compounds of formula (IIc) may be prepared from carboxylic acids of formula (IIb)

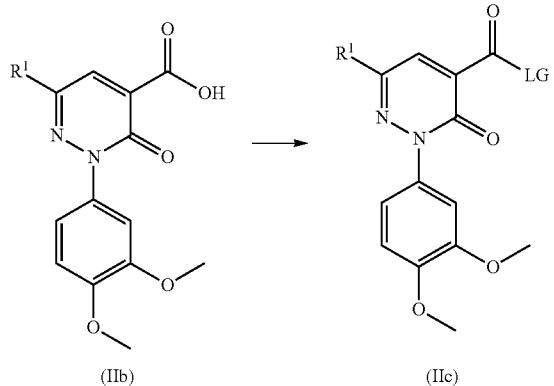

For example, for LG=chloro, the skilled person will recognize the common methods to execute this transformation such as treatment of the carboxylic acid with 1 equivalent of oxalyl chloride and a catalytic quantity of N,N-dimethylformamide in a non-polar solvent such as dichloromethane or acetonitrile.

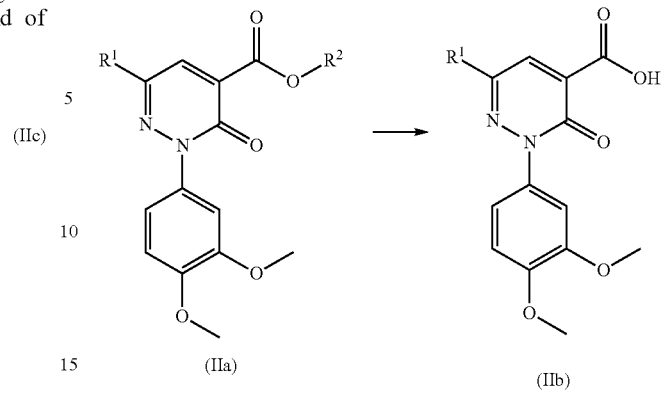

Carboxylic acids of Formula (IIb) may in turn be prepared from esters of Formula (Ia) by treatment with an alkoxide base such as lithium hydroxide in a suitable solvent system of a mixture of water and an organic solvent. Examples of suitable esters are wherein $R^2$ $C_1$-$C_6$alkyl-, such as methyl, ethyl, n-propyl and isopropyl. Examples of suitable solvent systems are tetrahydrofuran/water (1:1) or ethanol/water (1:1).

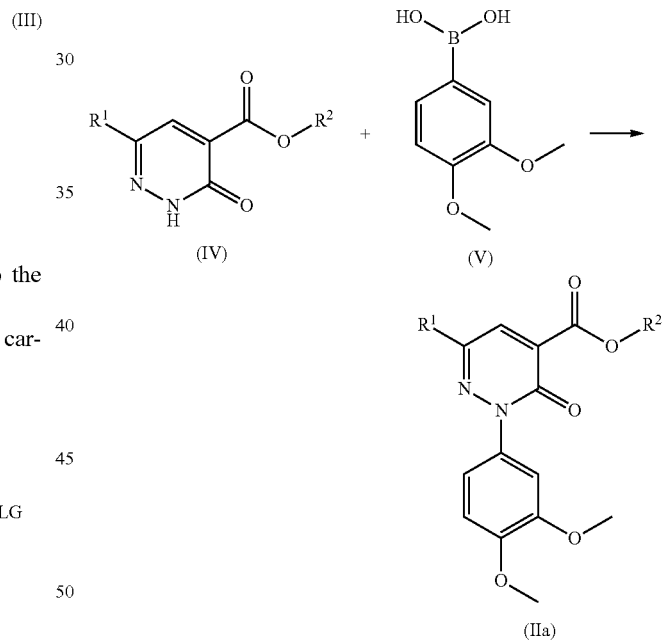

Esters of formula (IIa) may be prepared from the Chan-Lam coupling between pyridazinones of formula (IV) and 3,4-dimethoxyboronic solvent. Exacid. The Chan-Lam reaction is detailed in *Tetrahedron Lett.* 1998, 2933-2936. These reactions use a copper (II) or copper (I) salt such as copper (II) acetate, a non-polar solvent such as dichloromethane or 1,2-dichloroethane and an organic base, for example triethylamine or pyridine or a 1:1 mixture of triethylamine and pyridine. Super-stoichiometric equivalents of copper (I) or copper (II) salts, typically 1-3 equivalents of copper (II) acetate, may be used. Alternatively, catalytic amounts of the copper catalyst, for example 0.05 to 0.3 molar equivalents of copper (II) acetate, may be used instead if >1 equivalent of an oxidant is also added. Suitable examples of oxidants are pyridine-N-oxide or the bubbling of air or oxygen through the reaction mixture. The reaction can typically be performed at room temperature to achieve acceptable conversion in 2-16 h.

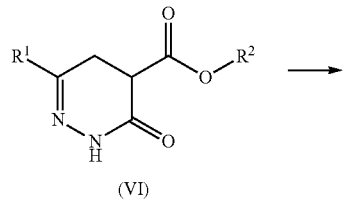

(VI)

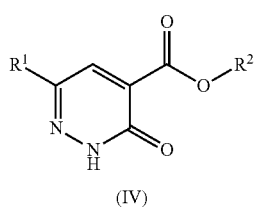

(IV)

Pyridazinones of formula (IV) may be prepared by the oxidation of dihydropyridazinones of formula (VI) with a suitable oxidising agent. Examples of suitable oxidising agents are bromine in a solution of acetic acid or dichloromethane, or iodobenzene diacetate in a solution of isopropanol.

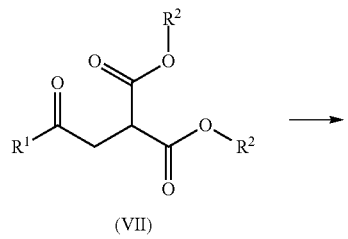

(VII)

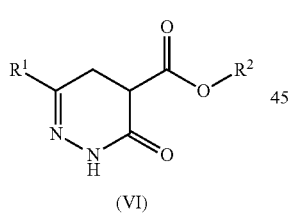

(VI)

Dihydropyridazinones of formula (VI) may be prepared through the treatment of compounds of formula (VII) with hydrazine hydrate in a suitable solvent such as ethanol under reflux conditions.

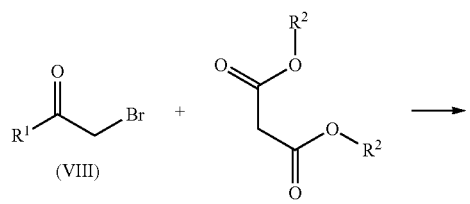

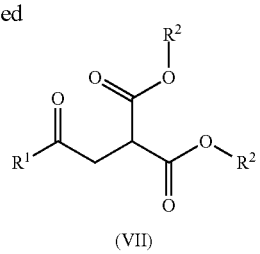

(VII)

Compounds of Formula (VII) may be prepared via the alkylation of a commercially available dialkyl malonate (for example diethyl malonate) with a bromo-ketone of Formula (VIII) in the presence of a suitable base, for example potassium carbonate, in a suitable solvent, for example acetone.

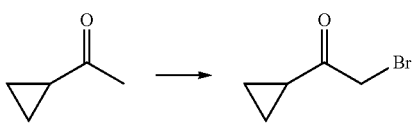

(IX) (VIII)

Compounds of Formula (VIII) may be commercially available, or alternatively they may be prepared via the bromination of a commercially available methyl ketone of Formula (IX) by treatment with bromine in a suitable solvent such as methanol or a mixture of water and glacial acetic acid (~5:1).

The following non-limiting examples provide specific synthesis methods for representative compounds of the present invention, as referred to in Table C1 above.

PREPARATIVE EXAMPLE 1

Preparation of 6-[6-cyclopropyl-2-(3,4-dimethoxyphenyl)-3-oxo-pyridazine-4-carbonyl]-2,2,4,4-tetramethyl-cyclohexane-1,3,5-trione (Compound 1.11 (See Table C1))

Step 1. Preparations of 2-Bromo-1-cyclopropyl-ethanone

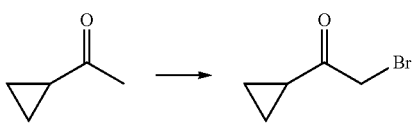

To a stirred solution of 1-cyclopropylethanone (50 g, 595 mmol) in MeOH (350 mL) at 0° C. (ice bath) was added bromine (32 mL, 595 mmol) dropwise over a period of 1 hour (the initial red colour of the reaction mixture became colourless by the end of the addition of bromine). The resulting solution was then stirred below 5° C. for 4 hours, then water (175 mL) was added and the reaction mixture stirred at room temperature for 16 hours. The reaction mixture was then poured into water (1000 mL) and extracted with CH$_2$Cl$_2$ (2×1000 mL). The combined organic layers was washed with saturated aqueous NaHCO$_3$ solution (500 mL), water (500 mL) and finally with brine (500 mL). The organic layer was dried over Na$_2$SO$_4$, filtered and concentrated in vacuo to give a light-brown oil. Pure 2-bromo-1- cyclopropyl-ethanone was obtained by vacuum distillation of this crude oil at 100° C. (59 g, 61%).

$^1$H NMR (400 MHz, CDCl$_3$) δ=4.01 (s, 2H), 2.22-2.17 (m, 1H), 1.14-1.11 (m, 2H), 1.03-0.99 (m, 2H).

Step 2. Preparation of diethyl 2-(2-cyclopropyl-2-oxo-ethyl)propanedioate

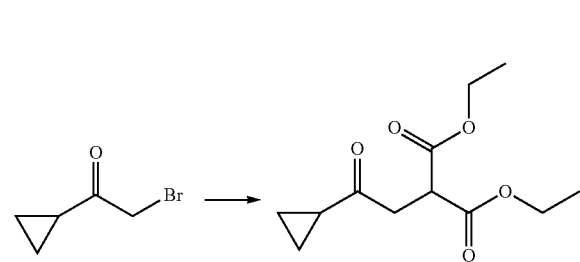 [SMILES: O=C(CBr)C1CC1 ; CCOC(=O)C(CC(=O)C1CC1)C(=O)OCC]

To a stirred solution of 2-bromo-1-cyclopropyl-ethanone (50 g, 307 mmol) in acetone (450 mL) at room temperature was added K$_2$CO$_3$ (64 g, 460 mmol), potassium iodide (1.5 g, 9.2 mmol) and diethylmalonate (54 g, 337 mmol) and the resulting mixture was heated at reflux (75° C.) for 16 hours. The reaction mixture was filtered and the filtrate concentrated in vacuo. The crude material was purified by column chromatography, eluting with 8% EtOAc in hexane to afford diethyl 2-(2-cyclopropyl-2-oxo-ethyl)propanedioate as a light yellow oil (40 g, 54%).

$^1$H NMR (400 MHz, CDCl$_3$) δ=4.24-4.13 (m, 4H), 3.95 (t, 1H), 3.18 (d, 2H), 1.98-1.92 (m, 1H), 1.26 (t, 6H), 1.06-1.03 (m, 2H), 0.93-0.88 (m, 2H).

Step 3. Preparation of ethyl 3-cyclopropyl-6-oxo-4, 5-dihydro-1H-pyridazine-5-carboxylate

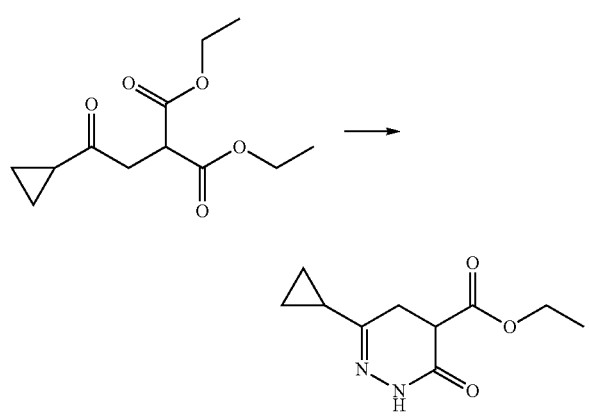

To a stirred solution of diethyl 2-(2-cyclopropyl-2-oxo-ethyl)propanedioate (70 g, 289 mmol) in EtOH (500 mL) between 0-5° C. (ice-water bath) was added hydrazine hydrate (16 mL, 318 mmol) dropwise and the resulting solution was stirred at room temperature for 20 hours. All volatiles were removed from the reaction mixture in vacuo to afford crude ethyl 3-cyclopropyl-6-oxo-4,5-dihydro-1H-pyridazine-5-carboxylate as a thick yellow oil (52 g, crude). This crude material was used in the next step without any further purification.

Step 4. Preparation of ethyl 3-cyclopropyl-6-oxo-1H-pyridazine-5-carboxylate

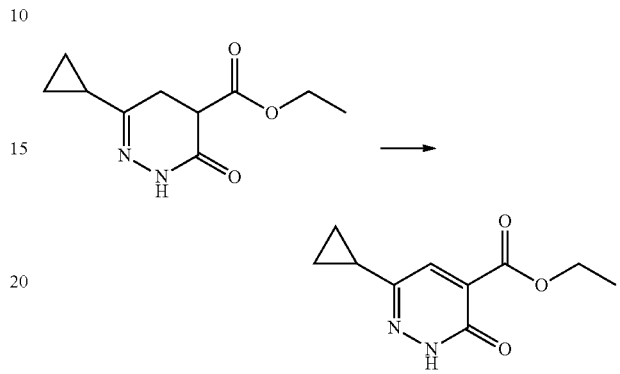

To a stirred solution of ethyl 3-cyclopropyl-6-oxo-4,5-dihydro-1H-pyridazine-5-carboxylate (52 g crude, 247 mmol) in AcOH (500 mL) between 10-15° C. was added a solution of bromine (20 mL, 317 mmol) in AcOH (200 mL) dropwise over a period of 30 minutes. The resultant solution was then stirred at room temperature for a further 30 minutes. The AcOH was removed from the reaction mixture in vacuo. To the residue was added EtOAc (2000 mL) and water (5000 mL) and the mixture shaken thoroughly. All insoluble particles were then removed by filtration through a Celite bed and then the filtrate layers were separated. The aqueous layer was extracted further with EtOAc (1000 mL). The combined EtOAc layers was then washed with saturated aqueous NaHCO$_3$ solution (500 mL), saturated aqueous Na$_2$S$_2$O$_3$ solution (500 mL) and finally with brine (500 mL). The organic layer was dried over Na$_2$SO$_4$, filtered and concentrated in vacuo. The crude material was purified by column chromatography eluting with 8% EtOAc in hexane to afford desired product as a light yellow solid. The solid was further purified by triturating with a 1% solution of EtOAc in hexane to afford ethyl 3-cyclopropyl-6-oxo-1H-pyridazine-5-carboxylate as an off white solid (17 g, 28% over two steps).

$^1$H NMR (400 MHz, CDCl$_3$) δ=11.17 (s, 1H), 7.65 (s, 1H), 4.40 (q, 2H), 1.92-1.85 (m, 1H), 1.38 (t, 3H), 1.02-0.98 (m, 2H), 0.92-0.88 (m, 2H).

Step 5. Preparation of ethyl 6-cyclopropyl-2-(3,4-dimethoxyphenyl)-3-oxo-pyridazine-4-carboxylate

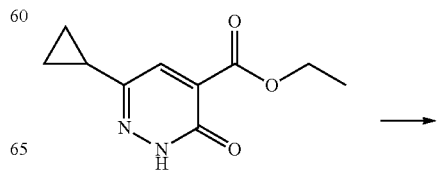

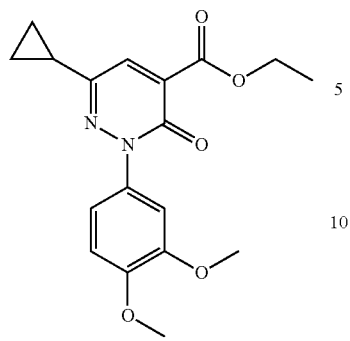

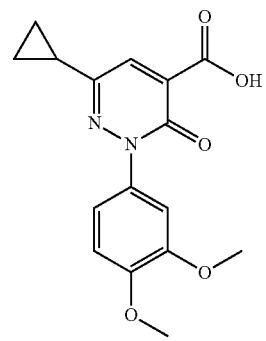

To a solution of ethyl 6-cyclopropyl-2-(3,4-dimethoxyphenyl)-3-oxo-pyridazine-4-carboxylate (2.40 g, 6.97 mmol) in tetrahydrofuran (50 mL) was added water (25 mL) followed by lithium hydroxide (0.45 g, 10.5 mmol). The resultant solution was stirred at room temperature for 90 minutes. The THF was removed in vacuo and the remaining aqueous mixture diluted with water (25 mL) and washed with EtOAc (30 mL). The vigorously stirred aqueous layer was acidified until pH=1 with conc. HCl solution—a yellow precipitate forms in the process. This was collected by filtration affording 6-cyclopropyl-2-(3,4-dimethoxyphenyl)-3-oxo-pyridazine-4-carboxylic acid as a yellow solid (1.78 g, 81%).

To a stirred solution of ethyl 3-cyclopropyl-6-oxo-1H-pyridazine-5-carboxylate (2.00 g, 9.61 mmol) in dichloromethane (70 mL) was added, 4 Å molecular sieves (0.88 g), copper(II) acetate monohydrate (4.01 g, 22.1 mmol), triethylamine (2.7 mL, 19.2 mmol) and pyridine (1.6 mL, 19.2 mmol). Then (3,4-dimethoxyphenyl)boronic acid (2.6 g, 14.4 mmol) was added portionwise over 10 minutes. The reaction mixture was stirred for 4 hours at room temperature with compressed air bubbling through. After 4 hours the compressed air was switched off and stirring continued for a further 16 hours. The reaction mixture was filtered through Celite washing the residue with additional CH$_2$Cl$_2$. The filtrate was washed with aqueous 2N HCl solution (2×100 mL) and saturated brine solution (100 mL). The organic layer was dried over MgSO$_4$, filtered and concentrated in vacuo to leave a dark yellow gum. Purification by column chromatography eluting with 0-100% EtOAc in isohexane afforded ethyl 6-cyclopropyl-2-(3,4-dimethoxyphenyl)-3-oxo-pyridazine-4-carboxylate as a bright yellow gum (2.46 g, 74%).

$^1$H NMR (400 MHz, CDCl$_3$) δ=14.10 (br. s, 1H), 8.06 (s, 1H), 7.14 (m, 1H), 7.10 (m, 1H), 6.97 (d, 1H), 3.95 (s, 3H), 3.90 (s, 3H), 2.10 (m, 1H), 1.15 (m, 2H), 1.00 (m, 2H).

Step 7. Preparation of 6-[6-cyclopropyl-2-(3,4-dimethoxyphenyl)-3-oxo-pyridazine-4-carbonyl]-2,2,4,4-tetramethyl-cyclohexane-1,3,5-trione (Compound 1.11)

$^1$H NMR (400 MHz, CDCl$_3$) δ=7.55 (s, 1H), 7.11 (m, 2H), 6.91 (d, 1H), 4.40 (q, 2H), 3.94 (s, 3H), 3.90 (s, 3H), 1.97 (m, 1H), 1.40 (t, 3H), 1.04 (m, 2H), 0.92 (m, 2H).

Step 6. Preparation of 6-Cyclopropyl-2-(3,4-dimethoxyphenyl)-3-oxo-pyridazine-4-carboxylic acid

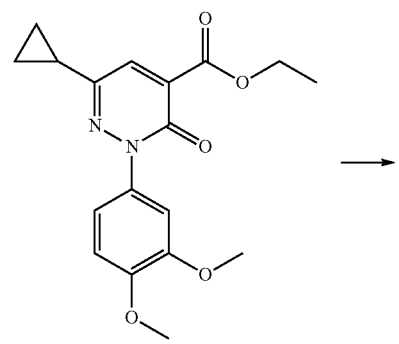

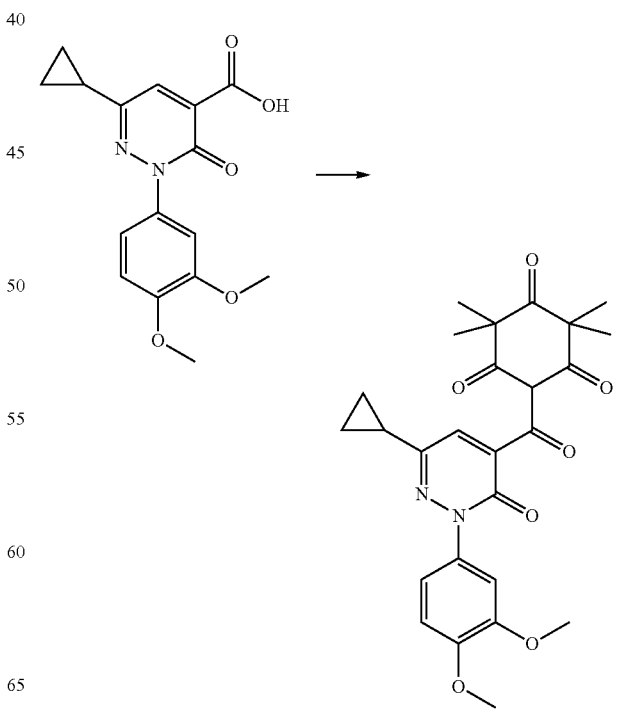

Under a nitrogen atmosphere, to a solution of 6-cyclopropyl-2-(3,4-dimethoxyphenyl)-3-oxo-pyridazine-4-carboxylic acid (1.00 g, 3.16 mmol) in dichloromethane (anhydrous, 20 mL) in a 100 mL 3-neck round bottom flask was added N,N-dimethylformamide (anhydrous, 0.012 mL, 0.158 mmol) followed by oxalyl chloride (0.29 mL, 3.32 mmol) dropwise and the reaction mixture stirred at room temperature for 1 hour. The reaction mixture was cooled to 0° C. (salt/ice bath) and triethylamine (1.77 mL, 12.7 mmol) was added dropwise over 15 minutes, then stirred for 5 minutes at 0° C. before 2,2,4,4-tetramethylcyclohexane-1,3,5-trione (0.58 g, 3.17 mmol) dissolved in minimum CH$_2$Cl$_2$ was added dropwise over 15 minutes. The resultant solution was stirred at 0° C. for 5 minutes then 1 hour at room temperature. The reaction mixture was cooled to 0° C. and further triethylamine (1.77 mL, 12.7 mmol) was added dropwise over 10 minutes followed by acetone cyanohydrin (0.044 mL, 0.475 mmol). The reaction mixture was stirred at 0° C. for 5 minutes then heated at reflux (40° C.) for 90 minutes. The reaction mixture was allowed to cool to room temperature, filtered and the filtrate concentrated in vacuo. Purification by column chromatography eluting with a mixed solvent system of 20:8:4:4:1 Toluene:Dioxane:EtOH:Et$_3$N:Water afforded the triethylamine salt of the desired compound. The crude oil was dissolved in MeOH and loaded onto a solid-phase-extraction SAX cartridge. The column was flushed with 3 column volumes of MeOH and then the desired product released with 1% formic acid in MeOH, concentrating in vacuo to afford 6-[6-cyclopropyl-2-(3,4-dimethoxyphenyl)-3-oxo-pyridazine-4-carbonyl]-2,2,4,4-tetramethyl-cyclohexane-1,3,5-trione (0.31 g, 20%) as a crushed orange foam.

$^1$H NMR (400 MHz, CDCl$_3$) δ=7.13 (s, 1H), 7.12-7.06 (m, 2H), 6.91 (d, 1H), 3.91 (s, 3H), 3.88 (s, 3H), 2.00-1.92 (m, 1H), 1.52 (br. s, 6H), 1.40 (br. s, 6H), 1.05-0.98 (m, 2H), 0.98-0.91 (m, 2H).

PREPARATIVE EXAMPLE 2

Preparation of 2-[6-cyclopropyl-2-(3,4-dimethoxyphenyl)-3-oxo-pyridazine-4-carbonyl]-5-methyl-cyclohexane-1,3-dione (Compound 1.8 (See Table C1))

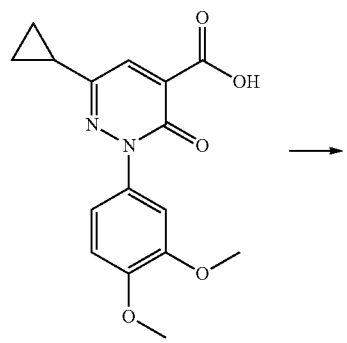

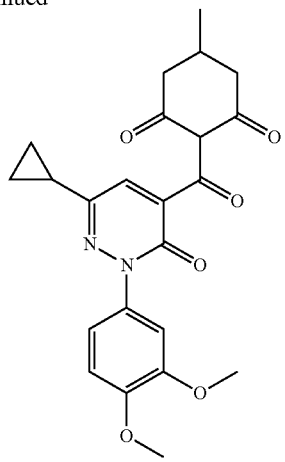

6-cyclopropyl-2-(3,4-dimethoxyphenyl)-3-oxo-pyridazine-4-carboxylic acid (1.00 g, 3.16 mmol) was taken in dry DCM (20 mL) and to it one drop of dry DMF was added. Then oxalylchloride (0.35 mL, 4.11 mmol) was added dropwise to the mixture & stirred for 1 h. The reaction mixture was concentrated under reduced pressure in nitrogen atmosphere. Then the crude reaction mass was dissolved in dry DCM (15 mL), activated molecular sieves was added & cooled the reaction mixture in ice salt bath. Then triethylamine (1.23 mL, 9.48 mmol) was added dropwise to the reaction mixture over 15 min. followed by 5-methyl-1,3-cyclohexane dione (479 mg, 3.79 mmol) in DCM (10 mL) was added dropwise to the reaction mixture. Stirred at room temperature for 1 h. Then triethylamine (1.23 mL, 9.48 mmol) and acetone cyanohydrin (0.22 mL, 2.37 mmol) were added and the reaction was stirred for 2.5 h. The crude was diluted with DCM & washed with 1 N HCl. Purification by column chromatography eluting with a mixed solvent system of 20:8:4:4:1 Toluene:Dioxane:EtOH:Et$_3$N:Water afforded the triethylamine salt of the desired compound as a brown gum. To this was added water (25 mL) and CH$_2$Cl$_2$ (25 mL) and this was acidified to pH 1 with 2M HCl. The mixture was stirred for 5 minutes, then the phases separated through a phase separation cartridge, washing with further CH$_2$Cl$_2$. The organic phase was concentrated to afford the desired product 2-[6-cyclopropyl-2-(3,4-dimethoxyphenyl)-3-oxo-pyridazine-4-carbonyl]-5-methyl-cyclohexane-1,3-dione (850 mg, 2.00 mmol, 63%) as a solid.

$^1$H NMR (400 MHz, CDCl$_3$) δ=7.14-7.10 (2H, m), 6.98 (1H, s), 6.89 (1H, d), 3.89 (3H, s), 3.87 (3H, s), 2.75-2.71 (1H, m), 2.53-2.39 (2H, m), 2.32-2.26 (1H, m), 2.18-2.12 (1H, m), 1.97-1.90 (1H, m), 1.08 (3H, d), 0.99-0.95 (2H, m), 0.93-0.87 (2H, m).

PREPARATIVE EXAMPLE 3

Preparation of 2-[2-(3,4-Dimethoxyphenyl)-6-methyl-3-oxo-pyridazine-4-carbonyl]cyclohexane-1,3-dione (Compound 1.3 (See Table C1))

Step 1. Preparation of 1-Bromopropan-2-one

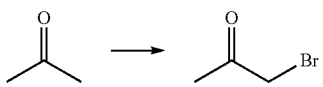

Acetone (150 g, 2.58 mol), water (480 mL) and glacial acetic acid (90 mL) were stirred in a two-necked round bottom flask and heated to reflux (75° C.). Bromine (73.2 mL, 2.84 mol) was added portionwise to the solution. The reaction mixture continued to be heated at 75° C. until it turned colourless. It was then cooled to 0° C. (ice-bath) and water added (100 mL) followed by sufficient $Na_2CO_3$ until it was no longer acidic. The reaction mixture was transferred to a separating funnel and the bottom organic layer separated, dried over $Na_2SO_4$ and filtered to afford 1-bromopropan-2-one (99.0 g, 28%).

$^1$H NMR (CDCl$_3$, 400 MHz) δ=3.23 (s, 2H), 1.67-1.72 (m, 3H).

Step 2. Preparation of diethyl 2-acetonylpropanedioate

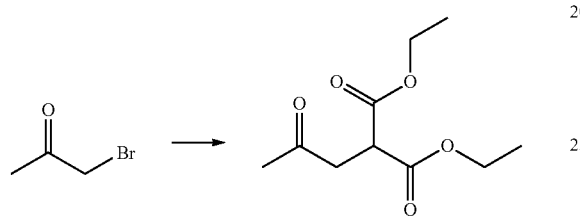

1-Bromopropan-2-one (90 g, 0.66 mol) was dissolved in acetone (740 mL) and under a nitrogen atmosphere diethylmalonate (126 mL, 0.79 mol), $K_2CO_3$ (136 g, 0.99 mol) and KI (3.27 g, 19.7 mmol) were added to the stirred solution. The reaction mixture was heated at reflux for 16 hours. The reaction mixture was filtered and the filtrate concentrated in vacuo. The crude material was dissolved in EtOAc and washed with water followed by brine. The organic layer was dried over $Na_2SO_4$, filtered and concentrated in vacuo to afford a liquid. This crude product was purified by column chromatography eluting with 0-5% MeOH in $CH_2Cl_2$ to afford diethyl 2-acetonylpropanedioate as a pale yellow oil (80.0 g, 56%).

$^1$H NMR (CDCl$_3$, 400 MHz) δ=4.21-4.04 (m, 4H), 3.78 (t, 1H), 2.99 (d, 2H), 2.20-2.06 (m, 3H), 1.27-1.13 ppm (m, 6H).

Step 3. Preparation of ethyl 3-methyl-6-oxo-4,5-dihydro-1H-pyridazine-5-carboxylate

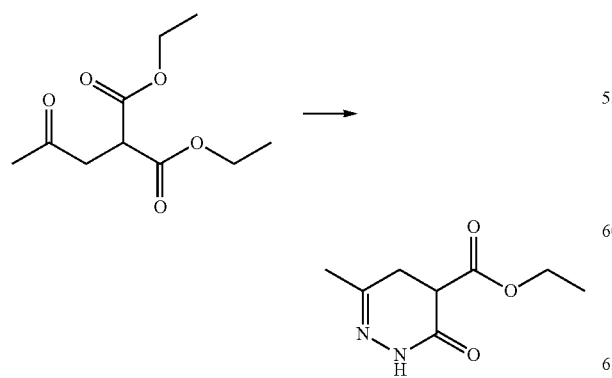

Diethyl 2-acetonylpropanedioate (80 g, 370 mmol) was dissolved in absolute ethanol (175 mL) and cooled to 0° C. To the stirred solution was added hydrazine hydrate (20.4 mL, 407 mmol) dropwise. The mixture was allowed to warm to room temperature and stirred for 16 hours. The reaction mixture was concentrated in vacuo and the resultant crude ethyl 3-methyl-6-oxo-4,5-dihydro-1H-pyridazine-5-carboxylate was used directly in the next step without further purification (61.0 g crude, 90%).

Step 4. Preparation of ethyl 3-methyl-6-oxo-1H-pyridazine-5-carboxylate

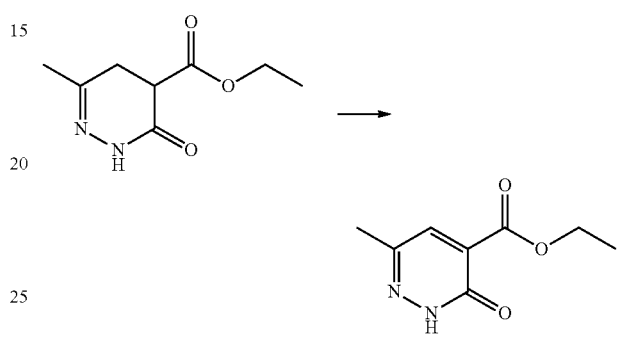

A solution of bromine (17 mL, 662 mmol) in acetic acid (140 mL) was added portion wise to a stirred solution of ethyl 3-methyl-6-oxo-4,5-dihydro-1H-pyridazine-5-carboxylate (61 g crude, 331 mmol) in acetic acid (1250 mL). The reaction mixture was stirred at room temperature for 1 hour then concentrated in vacuo. The crude material was dissolved in EtOAc and this solution washed with water followed by brine, dried over $Na_2SO_4$, filtered and concentrated in vacuo. The crude material was purified by column chromatography eluting with 0-5% MeOH in $CH_2Cl_2$ to afford ethyl 3-methyl-6-oxo-1H-pyridazine-5-carboxylate as an off-white solid (22.0 g, 37%).

$^1$H NMR (CDCl$_3$, 400 MHz) δ=7.71 (s, 1H), 4.40 (q, 2H), 2.39 (s, 3H), 1.39 (t, 3H).

Step 5. Preparation of ethyl 2-(3,4-dimethoxyphenyl)-6-methyl-3-oxo-pyridazine-4-carboxylate

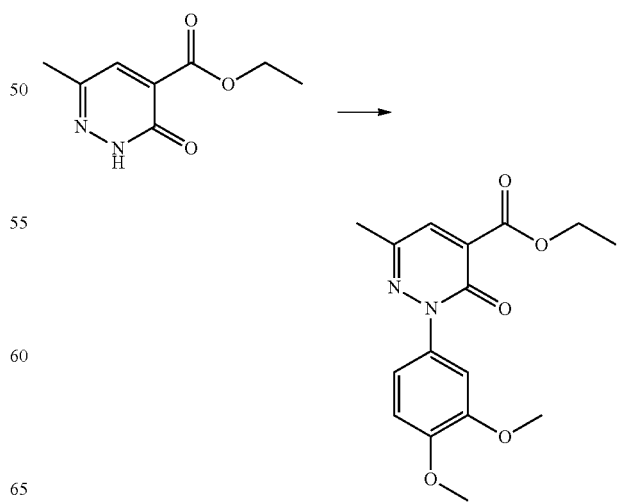

To a solution of ethyl 3-methyl-6-oxo-1H-pyridazine-5-carboxylate (5.0 g, 27.4 mmol) in dichloromethane (200 mL) was added copper(II) acetate monohydrate (12.6 g, 63.1 mmol), 4 Å molecular sieves, pyridine (4.4 mL, 54.9 mmol) and triethylamine (7.7 mL, 54.9 mmol). To the stirred suspension was added (3,4-dimethoxyphenyl)boronic acid (7.0 g, 38.4 mmol) portion wise over 5 minutes and the reaction mixture stirred at room temperature for 16 hours. The reaction mixture was filtered through Celite washing the residue with further $CH_2Cl_2$. The filtrate was washed with aqueous 2N HCl solution (2×200 mL), dried over $MgSO_4$, filtered and concentrated in vacuo. Purification by column chromatography eluting with 20-100% EtOAc in isohexane afforded ethyl 2-(3,4-dimethoxyphenyl)-6-methyl-3-oxo-pyridazine-4-carboxylate as a pale yellow solid (5.10 g, 58%).

$^1$H NMR (400 MHz, $CDCl_3$) δ=7.66 (s, 1H), 7.11 (br. s, 2H), 6.93 (d, 1H), 4.41 (q, 2H), 3.92 (s, 3H), 3.90 (s, 3H), 2.44 (s, 3H), 1.39 (t, 3H).

Step 6. Preparation of 2-(3,4-Dimethoxyphenyl)-6-methyl-3-oxo-pyridazine-4-carboxylic acid

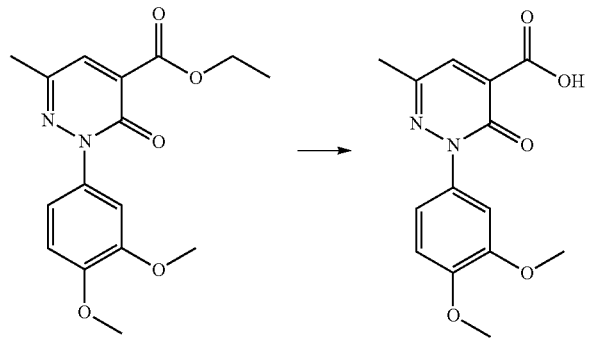

To a solution of ethyl 2-(3,4-dimethoxyphenyl)-6-methyl-3-oxo-pyridazine-4-carboxylate (12.0 g, 37.7 mmol) in tetrahydrofuran (200 mL) cooled to 0° C. (ice-bath) was added a solution of lithium hydroxide monohydrate (2.37 g, 56.5 mmol) in water (100 mL). The reaction mixture was allowed to warm to room temperature and stirred for 30 minutes. The THF was removed in vacuo and the aqueous mixture washed with $CH_2Cl_2$ (3×40 mL). The aqueous solution was cooled to 0° C., and stirred while conc. HCl solution was added until pH=1 was achieved. A bright yellow solid precipitated out in the process. This solid was collected by filtration. The solid was dissolved in $CH_2Cl_2$ and the solution dried over $MgSO_4$, filtered and concentrated in vacuo to afford 2-(3,4-dimethoxyphenyl)-6-methyl-3-oxo-pyridazine-4-carboxylic acid as a bright yellow solid (9.5 g, 87%).

$^1$H NMR (400 MHz, $CDCl_3$) δ=14.01 (br. s, 1H), 8.18 (s, 1H), 7.16 (d, 1H), 7.08 (br. s, 1H), 6.98 (d, 1H), 3.94 (app. d, 6H), 2.55 (s, 3H).

Step 7. Preparation of 2-[2-(3,4-Dimethoxyphenyl)-6-methyl-3-oxo-pyridazine-4-carbonyl]cyclohexane-1,3-dione (Compound 1.3)

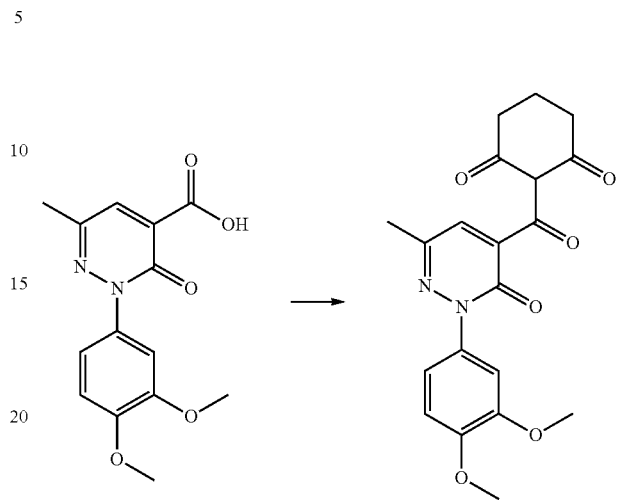

To a solution of 2-(3,4-dimethoxyphenyl)-6-methyl-3-oxo-pyridazine-4-carboxylic acid (1.00 g, 3.44 mmol) in dichloromethane (anhydrous, 13 mL) was added 3 drops of N,N-dimethylformamide (anhydrous) followed by dropwise addition of oxalyl chloride (0.33 mL, 3.79 mmol). The reaction mixture was stirred at room temperature for 16 hours. Further DMF (1 drop) and oxalyl chloride (0.1 mL) were added and stirring continued at room temperature for 1 hour. To a cooled (0° C. (ice bath)) solution of cyclohexane-1,3-dione (0.41 g, 3.62 mmol) in dichloromethane (anhydrous, 7.0 mL) was added triethylamine (1.44 mL, 10.3 mmol). The acid chloride solution was then added to the cyclohexane-1,3-dione-triethylamine solution via syringe pump over 10 minutes (70 mL/h) and the reaction mixture was stirred at 0° C. for a further 5 minutes. Further triethylamine (0.48 mL, 3.45 mmol) was added followed by acetone cyanohydrin (as a stock solution in anhydrous $CH_2Cl_2$) (10 mol %, 0.34 mmol). The reaction flask was transferred to a pre-heated oil bath and heated with stirring at reflux (40° C.) for 6 hours and then left stirring at room temperature for a further 16 hours. The reaction mixture was concentrated in vacuo to afford a black residue. Purification by column chromatography eluting with a mixed solvent system of 20:8:4:4:1 Toluene:Dioxane:EtOH:$Et_3N$:Water afforded the triethylamine salt of the desired compound as a brown gum. To this was added water (25 mL) and $CH_2Cl_2$ (25 mL) and this was acidified to pH 1 with 2M HCl. The mixture was stirred for 5 minutes, then the phases separated through a phase separation cartridge, washing with further $CH_2Cl_2$. The organic phase was concentrated to afford 2-[2-(3,4-dimethoxyphenyl)-6-methyl-3-oxo-pyridazine-4-carbonyl]cyclohexane-1,3-dione as an orange foam (400 mg, 30% yield).

$^1$H NMR (400 MHz, $CDCl_3$) δ=16.14 (1H, s), 7.13 (1H, dd), 7.09 (2H, m), 6.92 (1H, d), 3.90 (3H, s), 3.89 (3H, s), 2.73 (3H, t), 2.46 (3H, t), 2.41 (3H, s), 2.04 (2H, quintet).

PREPARATIVE EXAMPLE 4

Preparation of 3-[2-(3,4-dimethoxyphenyl)-6-methyl-3-oxo-pyridazine-4-carbonyl]bicyclo[3.2.1]octane-2,4-dione (Compound 1.1 (See Table C1))

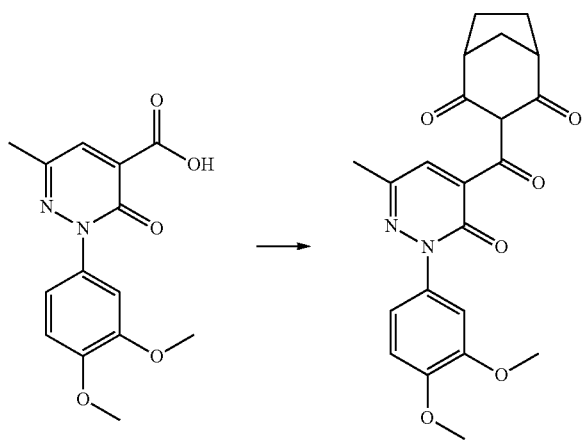

DMF (cat.) and oxalylchloride (0.6 mL) were added to a stirred suspension of 2-(3,4-dimethoxyphenyl)-6-methyl-3-oxo-pyridazine-4-carboxylic acid (1.5 g, 5.172 mmol) in DCM (20 mL). The reaction mixture was stirred at room temperature for 1.5 h. TLC (after quenching with MeOH) showed a non-polar spot formed. The reaction mass was evaporated under N2 atmosphere. DCM (20 mL) was added followed by a pinch of molecular sieve. TEA (2.2 mL) and bicyclo[3.2.1]octane-2,4-dione (0.86 g, 6.2 mmol) were added to acid chloride solution. The reaction mixture was stirred at room temperature for 1 h. Triethylamine (2.2 mL) and 25 drops of acetonecyanohydrin were added and stirred for 2 h. The reaction mass was purified by chromatography in with a mixed solvent system of 20:8:4:4:1 Toluene:Dioxane:EtOH:Et$_3$N:Water and then acidified by 10% HCl solution, extracted with DCM. The solvent was evaporated to get crude compound which was further purified by chromatography with acetone-DCM to afford the desired product 3-[2-(3,4-dimethoxyphenyl)-6-methyl-3-oxo-pyridazine-4-carbonyl]bicyclo[3.2.1]octane-2,4-dione (500 mg, 1.22 mmol, 24%) as a solid.

$^1$H NMR (400 MHz, CDCl$_3$) δ=16.19 (1H, s), 7.16-7.09 (3H, m), 6.93 (1H, d), 3.91 (6H, s), 3.11 (1H, t), 2.94 (1H, t), 2.42 (3H, s), 2.26-2.06 (3H, m), 2.04-1.98 (1H, m), 1.83 (1H, brm), 1.72 (1H, dt).

BIOLOGICAL EXAMPLES

Seeds of a variety of test species HORVW (*Hordeum vulgare*—barley), ABUTH (*Abutilon theophrasti*), AMARE (*Amaranthus retroflexus*) and ECHCG (*Echinochloa crus-galli*) were sown in standard soil in pots. After cultivation for 10 days cultivation under controlled conditions in a glasshouse (at 24/16° C., day/night; 14 hours light; 65% humidity), the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methyl pyrrolidone, 42.2% dipropylene glycol monomethyl ether (CAS RN 34590-94-8) and 0.2% X-77 (CAS RN 11097-66-8).

The test plants were then grown in a glasshouse under controlled conditions in a glasshouse (at 24/16° C., day/night; 14 hours light; 65% humidity) and watered twice daily. After 14 days, the test was evaluated (100=total damage to plant; 0=no damage to plant).

TABLE B1

| | | Plant Species | | | |
|---|---|---|---|---|---|
| Compound | Rate g/ha | HORVW | ECHCG | ABUTH | AMARE |
| 1.5 WO 2012/136703 | 250 | 50 | 90 | 90 | 90 |
| | 125 | 30 | 90 | 90 | 90 |
| 1.2 Present invention | 250 | 0 | 100 | 100 | 100 |
| | 125 | 0 | 100 | 100 | 100 |
| 1.3 WO 2012/136703 | 250 | 40 | 100 | 100 | 100 |
| | 125 | 30 | 100 | 100 | 100 |
| 1.3 Present invention | 250 | 0 | 100 | 100 | 100 |
| | 125 | 0 | 100 | 100 | 100 |

These comparative results demonstrate that the dimethoxyphenyl substituted pyridazinone compounds of the present invention are surprisingly less damaging to the crop plant (barley—HORVW) than the equivalent monomethoxyphenyl compounds specifically disclosed in WO 2012/136703, whilst retaining good control of representative weed species (ECHCG, ABUTH, AMARE).

TABLE B2

| | | Plant Species | | | |
|---|---|---|---|---|---|
| Compound | Rate g/ha | HORVW | ECHCG | ABUTH | AMARE |
| 1.1 | 250 | 0 | 100 | 100 | 100 |
| | 125 | 0 | 100 | 100 | 100 |
| 1.4 | 250 | 10 | 100 | 100 | 100 |
| | 125 | 0 | 100 | 100 | 100 |
| 1.5 | 250 | 0 | 90 | 100 | 100 |
| | 125 | 0 | 90 | 100 | 100 |
| 1.9 | 250 | 10 | 100 | 100 | 100 |
| | 125 | 0 | 100 | 100 | 90 |
| 1.11 | 250 | 0 | 100 | 100 | 100 |
| | 125 | 0 | 100 | 100 | 100 |

These results demonstrate that the compounds of the present invention confer little if any damage when applied to the crop plant (barley—HORVW) but still provide good control of representative weed species (ECHCG, ABUTH, AMARE).

The invention claimed is:
1. A compound of Formula (I):

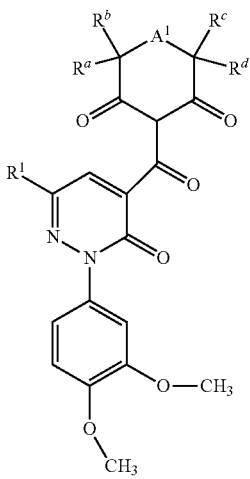

or an agronomically acceptable salt thereof,
wherein
$R^1$ is selected from the group consisting of hydrogen, halogen, cyano, nitro, $C_1$-$C_6$alkyl-, $C_3$-$C_6$cycloalkyl-, $C_2$-$C_6$-alkenyl-, $C_2$-$C_6$alkynyl-, $C_1$-$C_6$haloalkyl-, $C_1$-$C_6$alkoxy-, $C_1$-$C_3$haloalkoxy-, $C_1$-$C_6$alkoxy-$C_1$-$C_3$alkyl-, $C_1$-$C_6$alkyl-S(O)p- and $C_1$-$C_6$haloalkyl-S(O)p-;
$A^1$ is selected from the group consisting of O, C(O) and (CReRf);
$R^a$, $R^b$, $R^c$, $R^d$, $R^e$ and $R^f$ are each independently selected from the group consisting of hydrogen and $C_1$-$C_4$alkyl- wherein $R^a$ and $R^c$ may together form a $C_1$-$C_3$alkylene chain; and
p is 0, 1 or 2.

2. The compound according to claim 1, wherein $R^1$ is $C_1$-$C_6$alkyl- or $C_3$-$C_6$cycloalkyl-.

3. The compound according to claim 1, wherein $R^1$ is methyl or cyclopropyl-.

4. The compound according to claim 1, wherein $A^1$ is $CR^eR^f$ and $R^e$ and $R^f$ are hydrogen.

5. The compound according to claim 1, wherein $R^a$, $R^b$, $R^c$ and $R^d$ are hydrogen.

6. The compound according to claim 1, wherein $R^a$ and $R^c$ together form a —$CH_2$—$CH_2$— chain and $R^b$ and $R^d$ are hydrogen.

7. The compound according to claim 1, wherein $A^1$ is O and $R^a$, $R^b$, $R^c$ and $R^d$ are methyl.

8. The compound according to claim 1 in the form of an agrochemically acceptable salt, wherein the agrochemically acceptable salt is selected from the group consisting of aluminium, calcium, cobalt, copper, iron, magnesium, potassium, sodium and zinc.

9. A herbicidal composition comprising a compound according to claim 1 and an agriculturally acceptable formulation adjuvant.

10. A herbicidal composition according to claim 9, further comprising at least one additional pesticide.

11. A herbicidal composition according to claim 10, wherein the additional pesticide is a herbicide or herbicide safener.

12. A method of controlling weeds at a locus comprising application to the locus of a weed controlling amount of a composition according to claim 9.

13. A method of producing the compound of Formula (I) in claim 1 comprising:
(i) reacting, in an inert organic solvent and in the presence of a base, a compound of Formula (IIc):

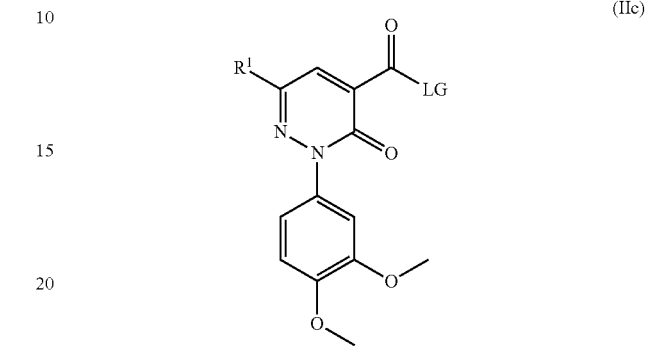

where the definition of $R^1$ is as for Formula (I) in claim 1 and LG is a suitable leaving group, with a diketone of Formula (III)

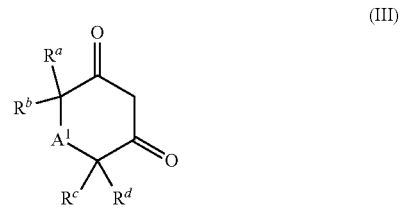

wherein $A^1$, $R^a$, $R^b$, $R^c$, and $R^d$ are as for Formula (I) in claim 1, and
(ii) rearrangement of the resulting product into the compound of Formula (I).

14. A compound of Formula (II)

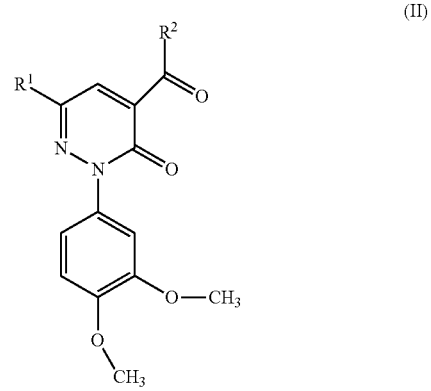

wherein
$R^1$ is selected from the group consisting of hydrogen, halogen, cyano, nitro, $C_1$-$C_6$alkyl-, $C_3$-$C_6$cycloalkyl-, $C_2$-$C_6$-alkenyl-, $C_2$-$C_6$alkynyl-, $C_1$-$C_6$haloalkyl-, $C_1$-$C_6$alkoxy-, $C_1$-$C_3$haloalkoxy-, $C_1$-$C_6$alkoxy-$C_1$-$C_3$alkyl-, $C_1$-$C_6$alkyl-S(O)p- and $C_1$-$C_6$haloalkyl-S(O)p-;

p is 0, 1 or 2; and
R$^2$ is selected from the group consisting of halogen, OH, C$_1$-C$_6$ alkoxy-, aryloxy and N-linked imdazolyl.

15. The compound according to claim 14, wherein R$^1$ is C$_3$-C$_6$cycloalkyl-, C$_2$-C$_6$-alkenyl-, C$_2$-C$_6$alkynyl-, C$_1$-C$_6$alkoxy-C$_1$-C$_3$alkyl-, C$_1$-C$_6$alkyl-S(O)p- and C$_1$-C$_6$haloalkyl-S(O)p-, and wherein p is 1 or 2.

16. The compound according to claim 14, wherein R$^1$ is methyl or cyclopropyl-.

17. The compound according to claim 16, wherein R$^2$ is selected from the group consisting of halogen, aryloxy and N-linked imdazolyl.

18. The compound according to claim 14, wherein R$^2$ is selected from the group consisting of halogen, aryloxy and N-linked imdazolyl.

19. The compound according to claim 14, wherein R$^1$ is C$_3$-C$_6$cycloalkyl-.

20. The compound according to claim 14, wherein R$^1$ is cyclopropyl.

* * * * *